US005549883A

United States Patent [19]

Srinivasan et al.

[11] Patent Number: 5,549,883

[45] Date of Patent: Aug. 27, 1996

[54] CHEMICALLY DEFINED POLYMERIC CARRIERS FOR RELEASE OF COVALENTLY LINKED AGENTS

[75] Inventors: Ananthachari Srinivasan, St. Charles, Mo.; Vivekananda M. Vrudhula, Edmonds; Diana I. Brixner, Lynnwood, both of Wash.

[73] Assignee: NeoRx Corporation, Seattle, Wash.

[21] Appl. No.: 71,357

[22] Filed: Jun. 3, 1993

Related U.S. Application Data

[63] Continuation of Ser. No. 765,126, Sep. 25, 1991, abandoned, which is a continuation-in-part of Ser. No. 590,086, Sep. 28, 1990, abandoned.

[51] Int. Cl.[6] .......................... A61K 51/08; A61K 49/00; C07K 1/00; C07K 2/00

[52] U.S. Cl. ........................ 424/1.45; 424/153; 424/1.69; 424/9.341; 530/333; 530/337; 530/300

[58] Field of Search ................................ 424/1.45, 1.53, 424/1.69, 9, 179.1, 181.1; 530/391.3, 391.5, 391.7, 391.9, 333, 345, 402, 807, 334, 335, 337, 300; 930/25, 30, 280; 534/10, 14, 15, 16

[56] References Cited

U.S. PATENT DOCUMENTS

| | | | |
|---|---|---|---|
| 4,485,093 | 11/1984 | Runge et al. | 424/85.91 |
| 4,543,211 | 9/1985 | Kato et al. | 260/112 |
| 4,587,046 | 5/1986 | Goodman et al. | 530/330 |
| 4,671,958 | 6/1987 | Rodwell et al. | 424/85.91 |
| 4,867,973 | 9/1989 | Goers et al. | 530/389 X |
| 4,906,452 | 3/1990 | Sivam | 424/85.91 X |
| 4,950,469 | 8/1990 | Katz | 424/85.1 |
| 4,952,394 | 8/1990 | Senter | 424/85.91 |
| 4,997,913 | 3/1991 | Hellstrom et al. | 424/85.91 x |
| 5,087,616 | 2/1992 | Myers et al. | 530/345 X |
| 5,094,848 | 3/1992 | Brixner | 530/345 X |
| 5,162,505 | 11/1992 | Dean et al. | 530/391.5 |
| 5,364,613 | 11/1994 | Sieving et al. | 424/9 |

FOREIGN PATENT DOCUMENTS

| | | | |
|---|---|---|---|
| 094844 | 5/1983 | European Pat. Off. . | |
| 0188256 | 7/1986 | European Pat. Off. . | |
| 253202 | 6/1987 | European Pat. Off. . | |
| 0284071 | 9/1988 | European Pat. Off. . | |
| 243121 | 12/1985 | Japan | 424/85.91 |
| 1541436 | 2/1979 | United Kingdom . | |
| 8705031 | 8/1987 | WIPO . | |
| 88/00837 | 2/1988 | WIPO . | |
| 88/03412 | 5/1988 | WIPO . | |

OTHER PUBLICATIONS

Torchlin et al., *Hybridoma*, vol. 6: pp. 229–240 (1987).

Ghose et al., *Methods in Enzymology*, vol. 93: pp. 280–333 (1983).

Haseman et al., *J. Nuclear Med.*, vol. 12: pp. 455–460 (1986).

Meares et al., *Int. J. Cancer* (Suppl. United States) vol. 2: pp. 99–102 (1988).

Deshpande et al., *Int. J. Rad. Appl. Instrum. (B) Eng.* vol. 16, No. 6; pp. 587–597 (1989).

R. V. Peterson, *Chemical Abstract*, vol. 94, No. 18, May 1981, Columbus, Ohio, Abstract No. 145233d, "Controlled release of progestins from poly(alpha–amino acid) carriers." p. 364.

J. C. Craig et al, *Chemical Abstract*, vol. 91, No. 12, Sep. 1979, Columbus, Ohio, Abstract No. 96584w, "Biological activity of isoproterenol covalently linked to synthetic polypeptides." p. 232.

W. A. R. Van Heeswijk et al, *Journal of Controlled Release*, vol. 1, No. 4, Jun. 1985, Amsterdam, Netherlands, "The synthesis and characterization of polypeptide–adriamycin conjugates and its complexes with adriamycin. part 1. " pp. 301–315.

*Primary Examiner*—Shean Wu
*Assistant Examiner*—Lara E. Chapman
*Attorney, Agent, or Firm*—Burns, Doane, Swecker & Mathis

[57] ABSTRACT

A chemically defined polymeric carrier comprising a series of α-amino acids in any combination containing side chains to which diagnostic/therapeutic and chelating agents can be covalently joined through cleavable linkers either directly or covalently joined through cleavable linkers after chemical modification of the side chains. Hydrazone, disulfide, and ester linkages in any combination can be present in the polymeric carrier between the side chains of the α-amino acids and the agents. The presence of a particular covalent linkage between the side chain and the agent in the carrier is determined by the functional group present in the side chain of the α-amino acid and the functional group present in the agent. The α-amino acids with side chains to which agents do not covalently join can function as spacers to minimize interaction between bulky molecules attached to the polymeric carrier. In addition, those α-amino acids with charged or hydrophilic side chains to which agents do not covalently join can provide increased solubility to the polymeric carrier.

10 Claims, 8 Drawing Sheets

Ac-Thr-Asp(β-COOTce)-Thr-Ser-Asp(β-COOTce)-Ser-Aba-OH

R = AGENT-OCO$(CH_2)_2$-

TFP-OH= 2,3,5,6-tetraflurophenol

Structure of the conjugate containing therapeutic drug attached to the defined peptide carrier attached to the antibody.

1(n=1),11(n=2),12(n=3)

13(n=1),14(n=2),15(n=3)

26 27 28 29 30

18

19

20

21

22

23

24 [Li'-H]

N-Acetyl-[L-Tyr-L-Asp-LGlu-Gly-LGlu]$_n$-γ-Aba-PAM resin 31 (n=2), 32 (n=3)

33 (n=2), 34 (n=3)

35 (n=2), 36 (n=3)

37 (n=2), 38 (n=3)

CHEMICALLY DEFINED POLYMERIC CARRIERS FOR RELEASE OF COVALENTLY LINKED AGENTS

This application is a continuation of application Ser. No. 07/765,126, filed Sep. 25. 1991, now abandoned, which is a continuation-in-part of application Ser. No. 07/590,086, filed Sep. 28, 1990, now abandoned.

BACKGROUND OF THE INVENTION

1. Field of the Invention

The invention relates to chemically defined polymeric carriers that provide advantageous properties for in vivo imaging and therapy. The polymeric carriers consist of α-amino acids that contain side chains covalently joined to (i) diagnostic and therapeutic molecules and (ii) chelating agents capable of binding diagnostic or therapeutic radionuclides.

2. Related Art

Monoclonal antibodies have been developed that localize in cancerous tissue, due to their high specificity and affinity for antigens on tumor cell surfaces. This development has increased the prospect of clinical applications, if such antibodies can be linked to diagnostic and therapeutic agents. The high specificity of the antibodies makes them desirable candidates as targeting molecules for delivering a diagnostic or therapeutic agent to a cancer site.

Unfortunately, the direct linkage of such agents to an antibody beyond an optimum level reduces its immunoreactivity and targeting ability. Any excessive derivatization results in lower immunoreactivity and targeting. In the present art, chelating agents capable of binding to diagnostic and therapeutic isotopes and cytotoxic agents are attached to antibodies in the following manner:

a) direct attachment to antibodies (e.g.) α-amino groups of lysine;

b) direct attachment to antibodies via cleavable linker; and c) the agents attached to a heterogeneous homopolymer such as polylysine, which in turn is attached to antibodies.

Direct attachment of therapeutic agents to proteins produces metabolities that have a high affinity to be excreted into the gut or retained by the kidney. In order to overcome this problem, the agents are attached via a clearable linker. This approach markedly reduces toxicity in the gut and kidney because of renal excretion of the agents. However, this procedure cannot deliver a therapeutic dose of such compounds. The use of polylysine as a carrier, while permitting an increased amount of therapeutic agents to be carried to the target, does not provide definition of product and is subject to variations. Since the linkage between the agent and carrier and the linkage between carrier and protein is less defined, rational variation of the rate of release of agents is not possible. Therefore, this approach precludes controlled release of a therapeutic molecule.

What is needed is an approach that derivatizes a targeting molecule such as an antibody or other proteins (growth factors) at a minimum number of sites to preserve high immunoreactivity and targeting ability. Such a procedure should be able to carry a therapeutic dose of a radionuclide-chelate or cytotoxic agent. Also needed, is an approach in which "chemically defined" polymers attached to antibodies carry therapeutic doses of agents from which the agent can be released in the native state to be efficacious. Such polymers attached to antibodies provide a complete definition of the product to meet the requirements of the regulatory process. By adjusting the "nature" of the "clearable linker" between therapeutic molecule and "chemically defined polymer" one can carry high doses of therapeutic molecules and release them at a desired site. Such a tailor-made "chemically defined" polymeric carrier unlike a heterogeneous homopolymer can incorporate functional groups to provide solubility. This is important when highly efficacious cytotoxic but lipid soluble drugs need to be employed.

SUMMARY OF THE INVENTION

The present invention provides a chemically defined polymeric carrier. It comprises a series of α-amino acids, in any combination, containing side chains to which diagnostic/therapeutic and chelating agents can be covalently joined through cleavable linkers. The agents can be covalently joined to the side chains through cleavable linkers either directly or covalently joined to the side chains through cleavable linkers after chemical modification of the side chains. Hydrazone, disulfide, and ester linkages, in any combination, can be present in the polymeric carrier between the side chains of the α-amino acids and the agents. The selection of a particular covalent linkage between the side chain and the agent in the polymeric carrier is determined by the functional group in the α-amino acid side chain and the reactive functional group in the agent. The α-amino acids with side chains to which agents do not covalently join can function as spacers, to minimize interaction between the bulky molecules attached to the polymeric carrier. In addition, those α-amino acids with charged or hydrophilic side chains to which agents do not covalently join can provide increased solubility to the polymeric carrier.

N-terminal protecting groups which are optional for the polymeric carrier include all the standard amine protecting groups. C-terminal conjugation groups which are optional for attachment of the polymeric carrier to the targeting molecule include all conjugation groups known in the art. In order to provide efficient attachment of the polymeric targeting molecule, a spacer group is present in the polymeric carrier between the α-amino acids and the conjugation group. The spacer group presents any steric hindrance to the attachment by any agent appended from the C-terminal end of the carrier. These spacer groups are terminal aminoacids, such as γ-aminobutyric acid (Aba). In the absence of the conjugation group, the spacer group, e.g., Aba through its carboxyl group, can attach the polymeric carrier to the targeting molecule.

The peptides that constitute the polymeric carrier are prepared from α-amino acids by conventional solution methods or by solid-phase peptide synthesis. These peptides have been modified to carry derivatized diagnostic/therapeutic agents, and chelating agents that bind to diagnostic and therapeutic radionuclides. These agents can be released either at the target site or after internalization by the cell.

Many advantages arise from the present invention. The polymeric carrier can carry a maximum number of agents while derivatizing a targeting molecule at a minimum number of sites. Thus the biological activity of the targeting molecule is maintained at a high level, even though it is attached to multiple agents. For example, the fewer the linkages in an antibody, the higher the retention of its specificity.

The rate at which agents can be released from the polymeric carrier attached to the targeting molecule is controlled by manipulating the nature of the covalent linkages in the polymeric carrier. For example, by adjusting the stability of the covalent linkages or by using different types of covalent linkages on a polymeric carrier, agents—are released at a mixed rate. This is particularly important when the disease requires use of long term sustained release of diagnostics or therapeutics.

Multiple agents, which may be the same or different, are attached to the polymeric carrier. Not only can the same agents be released at a mixed rate, but different agents can be released at a mixed rate in the same target site.

The polymeric carrier, with its covalently linked agents, is a relatively small molecule compared to the targeting molecule. Therefore, conventional detection techniques can predetermine the exact nature of the agent linkages to the targeting molecule before the polymeric carrier is attached to it. In addition, radiolabeling techniques can determine the precise number of polymeric carriers linked to the targeting molecule.

DETAILED DESCRIPTION OF THE INVENTION

Figure 1:
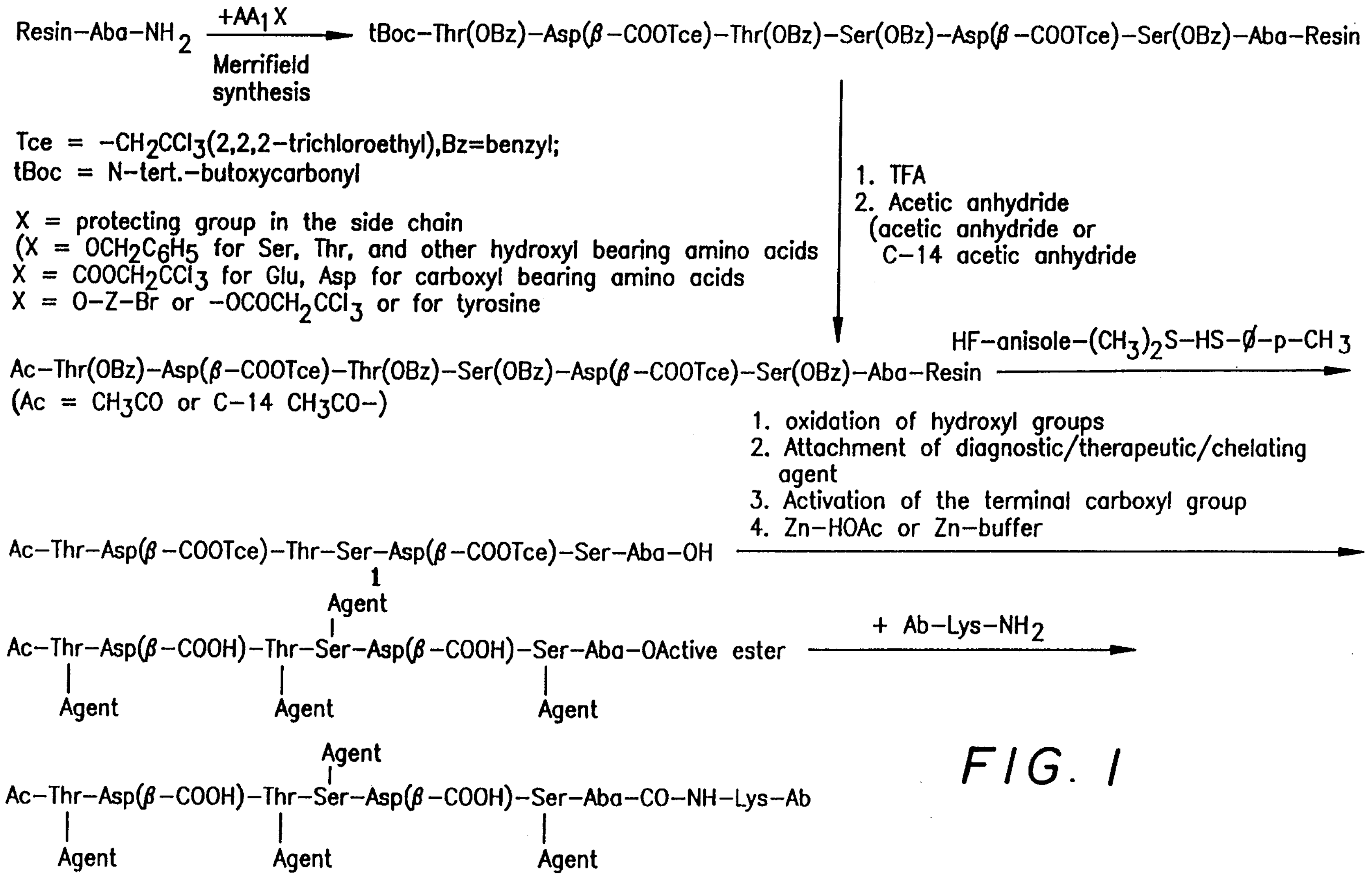
FIG. 1 [SEQ ID NOS.: 4–8] is a flow chart representing the general procedure for synthesis of a polymeric carrier with attached agents and the conjugation of the polymeric carrier to an antibody.

The present invention relates to a chemically defined polymeric carrier that increases the loading of diagnostic/therapeutic and chelating agents to targeting molecules. The polymeric carrier comprises a series of from 2 to about 18 α-amino acids in any combination that include side chains which can covalently join through cleavable linkers to agents. The number of agents covalently joined through clearable linkers to the polymeric carrier can be from 2 to about 18. This number is determined by the number of α-amino acid side chains in the polymeric carrier available for covalent bonding through cleavable linkers to the agents.

The term "polymeric carrier" as used in the invention denotes a peptide carrier. Those α-amino acids whose side chains are not covalently joined to agents can function as spacers for the polymeric carrier. These spacers reduce any non-bonded interactions between agents attached to modified α-amino acids. In addition to acting as spacers, those α-amino acids with charged or hydrophilic side chains not covalently joined to agents can impart increased solubility to the polymeric carrier.

The polymeric carrier includes optionally a protecting group at its N-terminal end and optionally a conjugation group at its C-terminal end. The conjugation group enables the polymeric carrier to attach itself to a targeting molecule. A spacer group is placed between the α-amino acids and the conjugation group to aid in the attachment of the polymeric carrier to the targeting molecule. The spacer group prevents any steric hindrance to the attachment by any agent appended from the C-terminal end of the carrier. In addition, the spacer group, a terminal amino acid, may attach the polymeric carrier to the targeting molecule without the presence of the conjugation group. This may occur by reacting the carboxyl group of the terminal amino acid with functional groups on the targeting molecule to form covalent bonds, such as ester and amide linkages.

In the polymeric carrier, α-amino acids having side chains that enhance polarity and therefore, water solubility, are desirable. The increased water solubility is believed to further contribute to decreased hepatobiliary uptake of radiolabeled polymeric carrier proteins. The α-amino acids having side chains that enhance water solubility include those with charged side chains (lysine, arginine, histidine, cysteine, aspartic acid, glutamic acid, tyrosine, tyrosine-O—$SO_3$—) and those with hydrophilic side chains (serine, threonine, asparagine, glutamine). Standard amine protecting groups can be used for the N-terminal protecting group of the polymeric carrier. Preferred embodiments of the invention comprise acetyl, proprionyl, phenylacylsulfonyl, substituted phenylacylsulfonyl, and other hydrophilic protecting groups.

A conjugation group is a chemically reactive functional group that will react with a targeting molecule to bind the polymeric carrier thereto. When the targeting molecule is a protein, the conjugation group is reactive under conditions that do not denature or otherwise adversely affect the protein. Therefore, the conjugation group is sufficiently reactive with a functional group on a protein so that the reaction can be conducted in a substantially aqueous solution and does not have to be forced, e.g., by heating to high temperatures, which may denature the protein. Examples of suitable conjugation groups include but are not limited to active esters, isothiocyanates, amines, hydrazines, maleimides or other Michael-type acceptors, thiols, and activated halides. Among the preferred active esters are N-hydroxysuccinimidyl ester, sulfosuccinimidyl ester, thiophenyl ester, 2,3,5,6-tetrafluorophenyl ester, and 2,3,5,6-tetrafluorothiophenyl ester. The latter three preferred active esters may comprise a group that enhances water solubility, at the para (i.e., 4) or the ortho position on the phenyl ring. Examples of such groups are $CO_2H$, $SO_3$—, $PO_3^{2-}$, $OPO_3^{2-}$, $OSO_3^-$, $N^+R_3$ wherein each R represents H or an alkyl group, and $O(CH_2CH_2O)_nCH_3$ groups.

Terminal amino acids used as spacer groups in the invent ion include aminocaproic acid, aminopentanoic acid, γ-aminobutyric acid, β-alanine, glycine, and the like.

Agents containing hydrazides, $R(CO)NHNH_2$, react with α-amino acid side chains containing aldehydes, RCHO, or ketones, $R_2(CO)$, to form polymeric carriers with hydrazone linkages having the following formula:

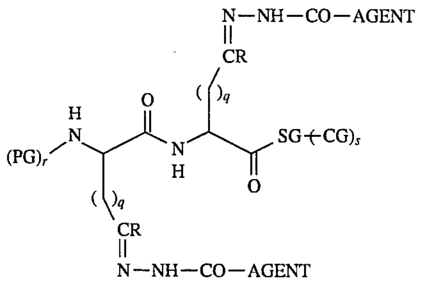

wherein

- the α-amino acids in the polymeric carrier are from 2 to about 18 units;
- PG is an N-terminal protecting group;
- SG is a spacer group that by preventing steric hindrance by agents appended from the C-terminal end of the carrier promotes efficient attachment of the polymeric carrier to a targeting molecule;
- CG is a conjugation group useful for the attachment of the polymeric carrier to a targeting molecule;
- AGENT is from 2 to about 18 units of a diagnostic or therapeutic agent, or a chelating agent capable of binding diagnostic or therapeutic radionuclides in the polymeric carrier;
- R is H, $CH_3$, phenyl, or phenyl substituted with electron-donating and/or electron-withdrawing groups;
- q is 0 or 1;
- r is 0 or 1; and
- s is 0 or 1.

Hydrazone formation is an effective method of attaching certain therapeutic agents to monoclonal antibodies (King et al., *Biochemistry*, Vol. 25:5774, 1986). Recent work in the area of therapeutic immunoconjugates addressed the hydrazone functionality as a potentially cleavable linker between a chemotherapeutic agent and a monoclonal antibody. Laguzza et al., (*J. Med. Chem.*, Vol. 32:548, 1989) demonstrated that a vinca alkaloid can be conjugated to an antibody via a hydrazone linkage and that pH dependency of the drug could be studied. The hydrazone linkage approach was based on the premise that a conjugate formed via a serum stable, yet acid-labile hydrazone linker would serve the purpose of delivering the drug conjugate to the tumor site and then slowly release upon exposure to the tumor's acidic environment (Tannock et al., *Cancer Research, Vol.* 49:4373, 1989). This conditional requirement necessitated the screening of several small molecule hydrazones to evaluate their stability in human serum and acetate buffer at pH 5.6.

The design of the polymeric carrier system with a hydrazone linkage incorporates the observed results of a small molecule study. Peptides of known amino acid sequences are constructed to carry primary or secondary hydroxyl groups (the chain may carry more than one hydroxy amino acid (primary or secondary), which can be oxidized to the carbonyl compound.

The results of the small molecule study indicate that hy drazones from aromatic aldehydes may be too stable to be useful. Hydrazones derived from aliphatic ketones have a serum half-life of 15–20 hours (generated in the peptides from threonine and other aminoacids containing secondary —OH groups). Hydrazones derived from aliphatic aldehydes (generated in the peptides from serine, homoserine and other amino acids containing primary —OH groups) have a serum half-life of 50–60 hours. Hydrazones derived from aromatic ketones (generated in the peptides from phenylserine and substituted phenylserines)) have a serum half-life of 130 hours. By choosing an antibody or its fragment with a half-life in human serum similar to that of hydrazone, maximum delivery of the antibody or its fragment to the tumor is expected. After which, the release of the therapeutic unit could occur at a rate dependent on the chosen hydrazone's half-life in the tumor site's or intracellular acidic environment. To prevent the polymeric carrier from possible premature degradation, the polymeric carrier can be constructed with only D-amino acids or a mixture of D- and L-amino acids.

Agents containing thiols, SH, react with cysteine side chains to form polymeric carriers with disulfide linkages having the following formula:

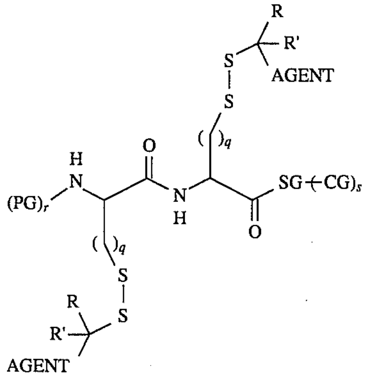

wherein

- the α-amino acids in the polymeric carrier are from 2 to about 18 units;
- PG is an N-terminal protecting group;
- SG is a spacer group that by preventing steric hindrance by agents appended from the C-terminal end of the carrier promotes efficient attachment of the polymeric carrier to a targeting molecule;
- CG is a conjugation group useful for the attachment of the polymeric carrier to a targeting molecule;
- AGENT is from 2 to about 18 units of a diagnostic or therapeutic agent, or a chelating agent capable of binding diagnostic or therapeutic radionuclides in the polymeric carrier;
- R is H or $CH_3$;
- R' is H or $CH_3$; and
- q is 1 or 2;
- r is 0 or 1; and
- s is 0 or 1.

The release rate for agents linked through disulfide bonds to the polymeric carrier can be decreased by replacement of hydrogen with α-alkyl groups ($R,R'=CH_3$).

Agents containing hydroxyl groups react with aspartic and glutamic acid side chains to form polymeric carriers with ester linkages having the following formula:

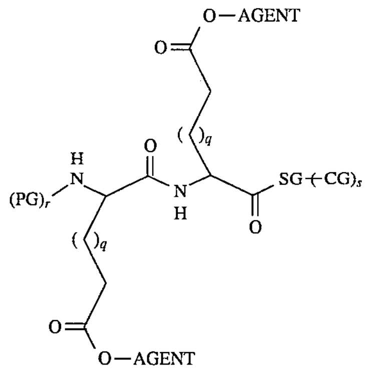

wherein the α-amino acids in the polymeric carrier 2 to about 18 units;

PG is an N-terminal protecting group;

SG is a spacer group that by preventing steric hindrance by agents appended from the C-terminal end of the carrier promotes efficient attachment of the polymeric carrier to a targeting molecule;

CG is a conjugation group useful for attachment of the polymeric carrier to a targeting molecule;

AGENT is from 2 to about 18 units of a diagnostic or therapeutic agent, or a chelating agent capable of binding diagnostic the or therapeutic radionuclides in the polymeric carrier;

q is 0 or 1;

r is 0 or 1; and s is 0 or 1.

In general, attachment of radionuclide metals (e.g., M=$^{99m}$Tc, $^{186}$Re or $^{188}$Re) to monoclonal antibodies using bifunctional chelating agent A has been carried out by the following procedure. Formation of M-chelate containing active ester B followed by attachment to monoclonal antibodies to give C, according to the following reaction scheme:

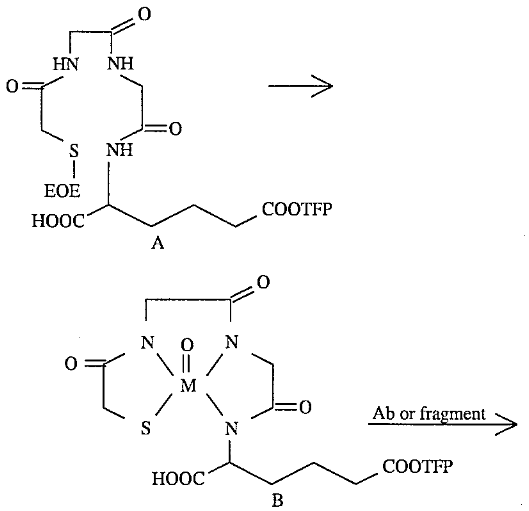

A

B

-continued

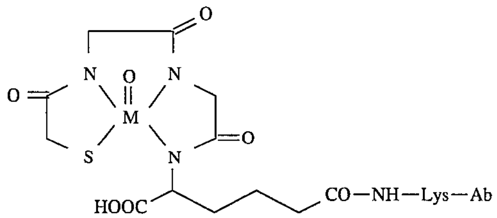

C

EOE refers to an ethoxy ethyl protecting group. COOTFP refers to 2,3,5,6-tetrafluorophenyl ester. The above chelate is an $N_3S$ derivative, and $N_2S_2$ derivatives follow a similar procedure. Between the chelate and the antibody is a carbon chain attached to the α-amino group of the antibody. After metabolism takes place in various organs, the major metabolite D is retained in the gut and kidney and is not excreted, according to the following:

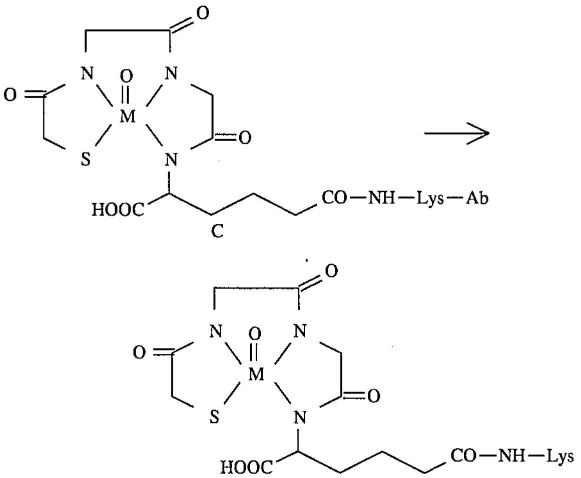

C

D

This retention interferes with imaging in the lower abdominal area and gives a high dose to the kidney during therapy. It was found that the presence of a cleavable linker between the chelate and the antibody (compound F, prepared from E) is metabolized and results in the formation of G, which has low excretion into the gut and low retention in the kidney, according to the following reaction scheme:

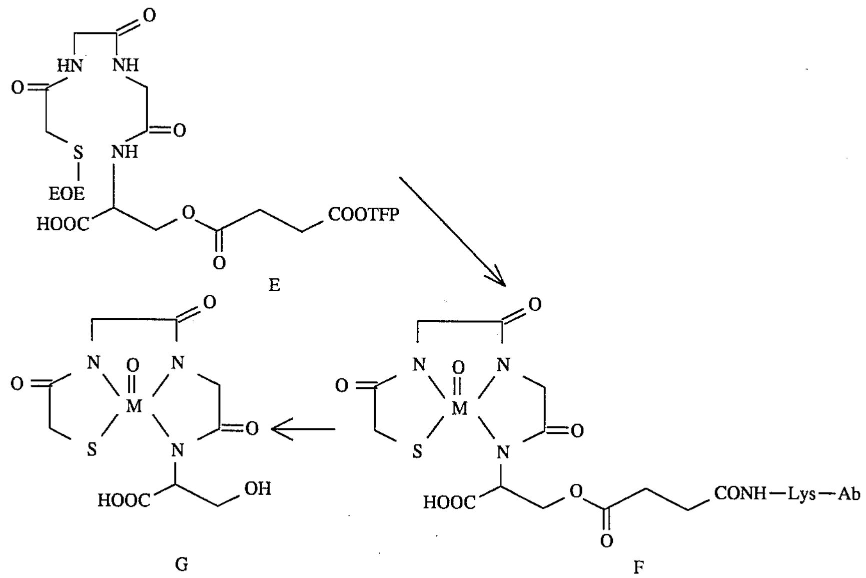

E

G

F

The observation that the clearable linker is metabolized in the above reaction scheme leads to attaching the hydroxy groups of the following compounds:

H

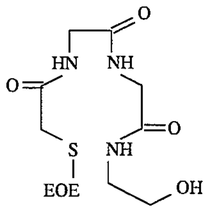

J

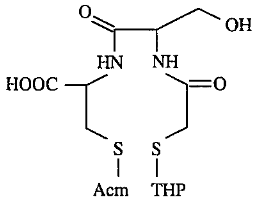

K

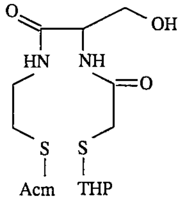

to the aspartic and glutamic acid side chains to form ester linkages in the polymeric carriers.

The resulting polymeric carrier can carry more than one radionuclide metal/per attachment to the antibody or fragment and offers the advantage of a metabolite that can be removed via the renal system instead of being retained in the gut.

Compound H belongs to $N_3S$ type chelates and J and K belong to the $N_2S_2$ chelate system. The groups THP (tetrahydropyranyl) and Acm (acetamidomethyl) are used as sulfur protecting groups.

The targeting molecule is any molecule that will serve to deliver the polymeric carrier with attached diagnostic/therapeutic or chelating agents to a desired target site (e.g., target cells) in vitro or in vivo. Examples of targeting molecules include, but are not limited to, steroids, cholesterol, lymphokines, and those drugs and proteins that bind to a desired target site.

The targeting molecule may be a targeting protein, which is capable of binding to a desired target site. The term "protein" as used herein includes proteins, polypeptides, and fragments thereof. The targeting protein may bind to a receptor, substrate, antigenic determinant, or other binding site on a target cell or other target site. The targeting protein serves to deliver the agent attached thereto by polymeric carrier to a desired target site in vivo. Examples of targeting proteins include, but are not limited to, antibodies and antibody fragments, hormones, fibrinolytic enzymes, and biologic response modifiers. In addition, other molecules that localize in a desired target site in vivo although not strictly proteins, are included within the definition of the term "targeting proteins" as used herein. For example, certain carbohydrates or glycoproteins may be used in the present invention. The proteins may be modified, e.g., to produce variants and fragments thereof, as long as the desired biological property (i.e., the ability to bind to the target site) is retained. The proteins may be modified by using various genetic engineering or protein engineering techniques.

Among the preferred targeting proteins are antibodies, most preferably monoclonal antibodies. A number of monoclonal antibodies that bind to a specific type of cell have been developed including monoclonal antibodies specific for tumor-associated antigens in humans. Among the many such monoclonal antibodies that may be used are anti-TAC, or other interleukin-2 receptor antibodies; 9.2.27 and NR-ML-05, reactive with the 250 kilodalton human melanoma-associated proteoglycan; and NR-LU-10, reactive with a pancarcinoma glycoprotein. The antibody employed in the present invention may be an intact (whole) molecule, a fragment thereof, or a functional equivalent thereof. Examples of antibody fragments are $F(ab')_2$, —Fab', Fab and $F_v$ fragments, which may be produced by conventional methods or by genetic or protein engineering.

Proteins contain a variety of functional groups; e.g., carboxylic acid (COOH) or free amine ($—NH_2$) groups, which are available for reaction with a suitable protein conjugation group on a polymeric carrier to bind the polymeric carrier to the targeting protein. For example, an active ester on the polymeric carrier reacts with epsilon amine groups on lysine residues of proteins to form amide bonds. Alternatively, a targeting molecule and/or a polymeric carrier may be derivatized to expose or attach additional reactive functional groups. The derivatization may involve attachment of any of a number of linker molecules such as those available from Pierce Chemical Company, Rockford, Ill. (See the Pierce 1986–87 General Catalog, pages 313–54.) Alternatively, the derivatization may involve chemical treatment of the protein (which may be an antibody). Procedures for generation of free sulfhydryl groups on antibodies or antibody fragments are also known. (See U.S. Pat. No. 4,659,839). Maleimide conjugation groups on polymeric carriers are reactive with the sulfhydryl (thiol) groups.

Alternatively, when the targeting molecule is a carbohydrate or glycoprotein, derivatization may involve chemical treatment of the carbohydrate; e.g., glycol cleavage of the sugar moiety of a glycoprotein antibody with periodate to generate free aldehyde groups. The free aldehyde groups on the antibody may be reacted with free amine or hydrazine conjugation groups on polymeric carriers.

In the present invention, therapeutic agents (e.g., a drug, therapeutic radionuclide or toxin) are attached to the chemically defined polymeric carrier. Preferably, multiple therapeutic agents (which may be the same or different) are attached to the polymeric carrier. Exemplary therapeutic agents include toxins and drugs. Within the present invention, preferred toxins include holotoxins, such as abrin, ricin, modecin, Pseudomonas exotoxin A; Diphtheria toxin, pertussis toxin and Shiga toxin; and A chain or "A chain-like" molecules, such as ricin A, abrin A chain, modeccin A chain, the enzymatic portion of pertussis toxin, the enzymatic portion of Shiga toxin, gelonin, pokeweed antiviral protein, saporin, barley toxin, and snake venom peptides.

Exemplary drugs include daunomycin, adriamycin, vinblastine, doxorubicin, bleomycin, methotrexate, 5-fluorouracil, 6-thioguanine, cytarabine, cyclophosphamide, and similar conventional chemotherapeutics (for example, see *Cancer: Principles and Practices of Oncology,* 2d ed., V. T. DeVita, Jr., S. Hellman, S. A. Rosenberg, J. B. Lippincott Co., Philadelphia, Pa., 1985, Chapter 14). Yet other preferred drugs that can be used with the present invention belong to the tricothecene family, with Roridin A particularly preferred. Experimental drugs may also be suitable for used within the present invention (see, e.g., *NCI Investigational Drugs Pharmaceutical Data* 1987, NIH Publication No. 882141, Revised November 1987).

In the present invention, radiolabeled molecules are attached to the chemically defined polymeric carrier. Preferably, a multiple No. of radiolabeled molecules (which may be the same or different) are attached to the polymeric carrier.

Radionuclide metal chelates are one type of radiolabeled molecule that may be employed. Many chelating compounds of various structures, as well as methods for the synthesis and radiolabeling thereof to produce radionuclide metal chelates, are known. Chelating compounds comprising various combinations of sulfur, nitrogen, oxygen, and phosphorous donor atoms may be used, for example. The chelating compound may, for example, comprise a total of from four to six donor atoms selected from nitrogen and sulfur atoms. During the radiolabeling procedure, bonds form between the donor atoms and the radionuclide metal, thereby producing a radionuclide metal chelate. Chelating compound(s) may be incorporated into the polymeric carrier during the synthesis procedure. Alternatively, the chelating compound(s) may be synthesized separately and subsequently attached to the polymeric carrier.

The mechanism of cell kill occurs by a different mode of action for radioactive metal-chelates than for non-radioactive cytotoxic agents. In both cases, a metal-chelate or free therapeutic agent is released. While a therapeutic agent imparts its action by interaction with the DNA or RNA synthesis process, such a mechanism is not essential for a radioisotope chelate. Hence, design of chelates is crucial for this methodology. All chelates employed carry one or preferably more negative charges for tumor retention if the chelate is released intracellularly.

One type of chelating compound that may be employed comprises two nitrogen and two sulfur donor atoms and thus may be designated an "$N_2S_2$" chelating compound. Suitable $N_2S_2$ chelating compounds are described in U.S. Pat. No. 4,897,255, entitled "Metal Radionuclide Labeled Proteins for Diagnosis and Therapy" which is hereby incorporated by reference in its entirety. One example of 20 an $N_2S_2$ chelating compound is as follows:

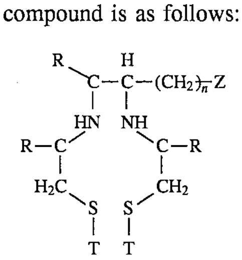

wherein n is from 1 to about 4 (preferably 2); each R independently is selected from =O and $H_2$; T represents a sulfur protecting group; and Z represents an active ester or other reactive functional group (which in the present invention may be useful for incorporating the chelating compound into the polymeric carrier).

Any suitable conventional sulfur protecting group(s) may be attached to the sulfur donor atoms of the compounds of the present invention. The protecting groups should be removable, either prior to or during the radiolabeling reaction. Among the preferred sulfur protecting groups are Acm and hemithioacetal protecting groups (EOE, THP), which are displaceable from the chelating compound during the radiolabeling reaction.

The $N_2S_2$ chelating compound advantageously is radiolabeled after attachment to the polymeric carrier to produce a radionuclide metal chelate of the formula:

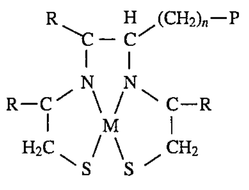

wherein P represents the polymeric carrier, M represents a radionuclide metal or oxide thereof, and the other symbols are as described above.

Radionuclide metals include, but are not limited to, the diagnostically effective radionuclide $^{99m}$Tc, and the therapeutically effective radionuclides $^{188}$Re, $^{186}$Re, $^{67}$Cu, $^{64}$Cu, $^{212}$Pb, $^{212}$Bi, and $^{109}$Pd. $^{186}$Re and $^{188}$Re are radionuclide metals for use in the present invention.

Methods for preparing these isotopes are known. Molybdenum/technetium generators for producing $^{99}$Tc are commercially available. Procedures for producing $^{186}$Re include the procedures described by Deutsch et al., (*Nucl. Med. Biol.,* Vol. 13:4:465–477, 1986) and Vanderheyden et al., (*Inorganic Chemistry,* Vol. 24:1666–1673, 1985), and $^{222}$Bi methods for production of $^{188}Re$ have been described by Blachot et al. (*Intl. J. of Applied Radiation and Isotopes,* Vol. 20:467–470, 1969) and by Klofutar et al. (*J. of Radioanalytical Chem.,* Vol. 5:3–10, 1970). Production of $^{109}Pd$ is described in Fawwaz et al., *J. Nucl. Med.* (1984), 25:796. Production of $^{212}Pb$ and $^{222}Bi$ is described in Gansow et al., *Amer. Chem. Soc. Symp. Ser.* (1984), 241:215–217, and *Kozah et al., Proc. Nat'l. Acad. Sci.* USA (January 1986) 83:474–478.

The radiolabeling reaction (for this $N_2S_2$ compound and the other chelating compounds described below) is conducted using conventional procedures.

Additional $N_2S_2$ chelating compounds comprising carboxylic acid substituent(s) for improved biodistribution properties are described in copending U.S. patent application Ser. No. 07/367,502, now abandoned, entitled "Radionuclide Metal Chelates for the Radiolabeling of Proteins", which is hereby incorporated by reference Examples of such chelating compounds are as follows:

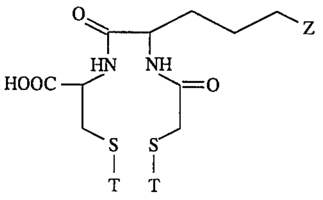

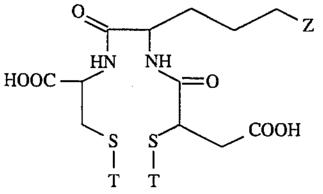

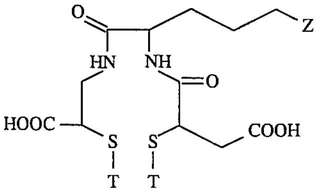

-continued

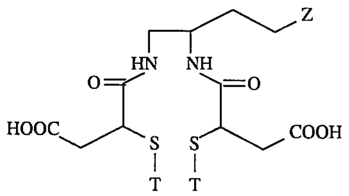

wherein the symbols T and Z are as described above for the other $N_2S_2$ chelating compounds.

Another type of chelating compound that may be employed comprises one sulfur and three nitrogen donor atoms and thus may be designated an "$N_3S$" chelating compound Suitable $N_3S$ chelating compounds include those described in European patent application publication number 284,071 and copending U.S. patent application Ser. No. 07/172,004, now U.S. Pat. No. 4,965,392, both entitled "Metal-Radionuclide-Labeled Proteins and Glycoproteins for Diagnosis and Therapy", which are hereby incorporated by reference in their entirety. Examples of $N_3S$ chelating compounds include but are not limited to the following seven compounds, wherein "T" represents a sulfur protecting group and "COOTFP" represents a 2,3,5,6-tetrafluorophenyl ester group:

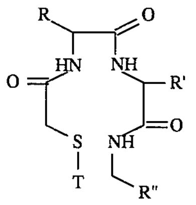

| | R | R' | R'' |
|---|---|---|---|
| Compound 1 | H | H | $CH_2-CH_2-COOTFP$ |
| Compound 2 | $CH_2-COOH$ | H | $CH_2-CH_2-COOTFP$ |
| Compound 3 | $CH_2-COOH$ | $CH_2-COOH$ | $CH_2-CH_2-COOTFP$ |
| Compound 4 | $CH_2-CH_2-COOH$ | $CH_2-COOH$ | $CH_2-CH_2-COOTFP$ |
| Compound 5 | H | $CH_2-CH_2-COOTFP$ | COOH |
| Compound 6 | $CH_2-CH_2-CH_2-COOTFP$ | H | COOH |
| Compound 7 | H | H | $CH_2-CH_2-COOTFP$ |

The COOTFP active ester may be replaced by other chemically reactive functional groups.

Other chelating compounds may have different combinations of donor atoms. Such compounds include among others, the $N_2S_4$, $N_2S_3$, and $N_3S_3$ chelating compounds described in copending U.S. patent application Ser. No. 07/201,134, now U.S. Pat. No. 4,988,496, entitled "Metal Radionuclide Chelating Compounds for Improved Chelation Kinetics", which is hereby incorporated by reference in its entirety. In addition, the $N_2S_2$ and $N_3S$ compounds presented above may comprise varying numbers of substituents such as carboxylic acid groups and from 0 to 3 oxygen atoms (=O) attached to carbon atoms of the chelate core.

In the present invention, the chelating compounds comprise, or are attached to, cleavable linkers. A number of linkers that are cleavable under defined conditions (e.g., at acidic pH, under reducing conditions, or in the presence of an enzyme such as a protease) are known. The chelates therefore may be released from the polymeric carrier under the desired conditions.

Suitable chelating compounds comprising a cleavable link age include but are not limited to those described in copending U.S. patent application Ser. No. 07/457,480, now U.S. Pat. No. 5,112,953, entitled "Radiolabeled Proteins for Diagnostic and Therapeutic Use", which is hereby incorporated by reference in its entirety. The U.S. Ser. No. 07/457, 480 application, now U.S. Pat. No. 5,112,953, discloses $N_2S_2$ and $N_3S$ chelating compounds comprising a linker of defined structure that terminates in a chemically reactive functional group. The linkage is clearable at an ester group positioned in a particular orientation therein. Examples of such chelating compounds include, but are not limited to, the following:

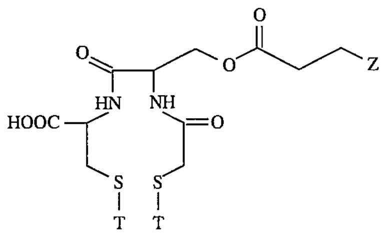

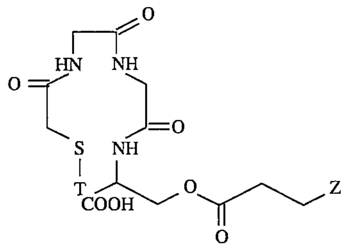

-continued

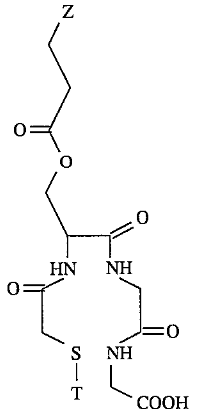

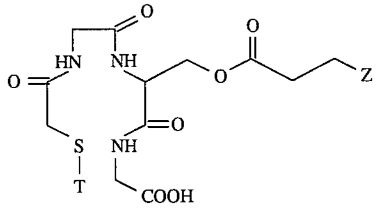

wherein T represents a sulfur protecting group and Z represents a chemically reactive group (e.g., an active ester) which may be used to incorporate the chelating compound into the polymeric carrier in accordance with the present invention.

Other examples of radiolabeled molecules that may be attached to the polymeric carrier in accordance with the present invention include radiohalogenated molecules. Examples of molecules that bind radiohalogens at the meta or para position on a phenyl ring are described in U.S. Pat. No. 4,855,153, entitled "Radiohalogenated Proteins", which is hereby incorporated by reference in its entirety. These compounds may be represented by the following formula:

*X—Ar—R wherein

*X is a radioisotope of iodine, bromine, fluorine, or astatine;

Ar is an aromatic or heteroaromatic ring; and

R is a chemical bond or a substituent containing 1 to 12 straight-chain carbon atoms that does not activate Ar toward electrophilic substitution on the order produced by hydroxy or amino substitution of the ring. The bond or substituent has attached thereto a chemically reactive functional group useful in the present invention for incorporation of the compound (or a non-radiolabeled precursor thereof) onto the polymeric carrier.

*I-paraiodophenyl compounds (in which *I represents a radioisotope of iodine) may be prepared using procedures that generally involve substituting the organometallic group Sn(n-Bu)$_3$ or SnMe$_3$ on a haloaromatic compound. A radioisotope of a halogen then is substituted for the organometallic group by halodemetalization. Examples of radiohalogenated molecules that may be prepared using such a procedure are represented by the following formulas:

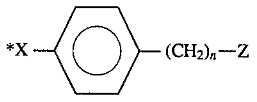

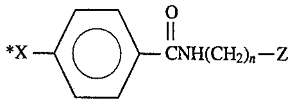

wherein n represents an integer from 0 to 3, Z represents a reactive functional group, and *X represents a radioisotope of a halogen.

Additional radiohalogenated molecules that may be used in the present invention are described in U.S. Pat. No. 4,876,081, which is hereby incorporated by reference in its entirety. The radiohalogenated molecules comprise a vinyl group.

The radiolabeled polymeric carrier targeting molecules of the present invention have use in diagnostic and therapeutic procedures, both for in vitro assays and for in vivo medical procedures. The radiolabeled polymeric carrier molecules may be administered intravenously, intraperitoneally, intralymphatically, locally, or by other suitable means, depending on such factors as the type of target site. The amount to be administered will vary according to such factors as the type of radionuclide (e.g., whether it is a diagnostic or therapeutic radionuclide), the route of administration, the type of target site(s), the affinity of the targeting molecule for the target site of interest, and any cross-reactivity of the targeting molecule with normal tissues.

Appropriate dosages may be established by conventional procedures and a physician skilled in the field to which this invention pertains will be able to determine a suitable dosage for a patient. A diagnostically effective dose is generally from about 5 to about 35 mCi and typically from about 10 to about 30 mCi per 70 kg body weight. A therapeutically effective dose is generally from about 20 mCi to about 300 mCi. For diagnosis, conventional non-invasive procedures (e.g., gamma cameras) are used to detect the biodistribution of the diagnostic radionuclide, thereby determining the presence or absence of the target sites of interest (e.g., tumors).

To render the ester in the polymeric carrier molecules of the present invention more susceptible to cleavage in the kidneys, an agent that raises urine pH may also be administered to the patient. Such agents include, for example, a salt of ascorbate (e.g., sodium ascorbate) or a bicarbonate salt (e.g., sodium bicarbonate), which may be administered intravenously. Raising the urine pH to a basic level promotes cleavage of the ester in conjugates or catabolites thereof localized in the kidneys. Clearance of the released radionuclide metal chelates from the body is thereby enhanced. Administration of such agents to promote cleavage of ester linkers in vivo is described in U.S. patent application Ser. No. 07/251,900, now abandoned, which is hereby incorporated by reference.

The comparatively low intestinal localization of the therapeutic radiolabeled polymeric carrier antibodies of the present invention or catabolites thereof permits increased dosages, since intestinal tissues are exposed to less radiation. The clarity and accuracy of diagnostic images also is improved by the reduced localization of radiolabeled polymeric carrier antibodies or catabolites thereof in normal tissues.

The above disclosure generally describes the present invention. A more complete understanding can be obtained by reference to the following specific examples which are provided for purposes of illustration only, and are not intended to limit the scope of the invention.

EXAMPLE 1

Three peptide carriers containing 6, 12, and 18 α-amino acids with different side chain hydroxyl groups are synthesized to show the use of hydrazones in covalently linking to agents. The requisite peptides are synthesized using the solid phase methodology of Merrifield (G. Barany and R. B; Merrifield, "The Peptides. Analysis, Synthesis and Biology" E. Gross and J. Meinhofer, Editors, Academic Press, New York, pages 1–284 (1980).

Figure 2A:
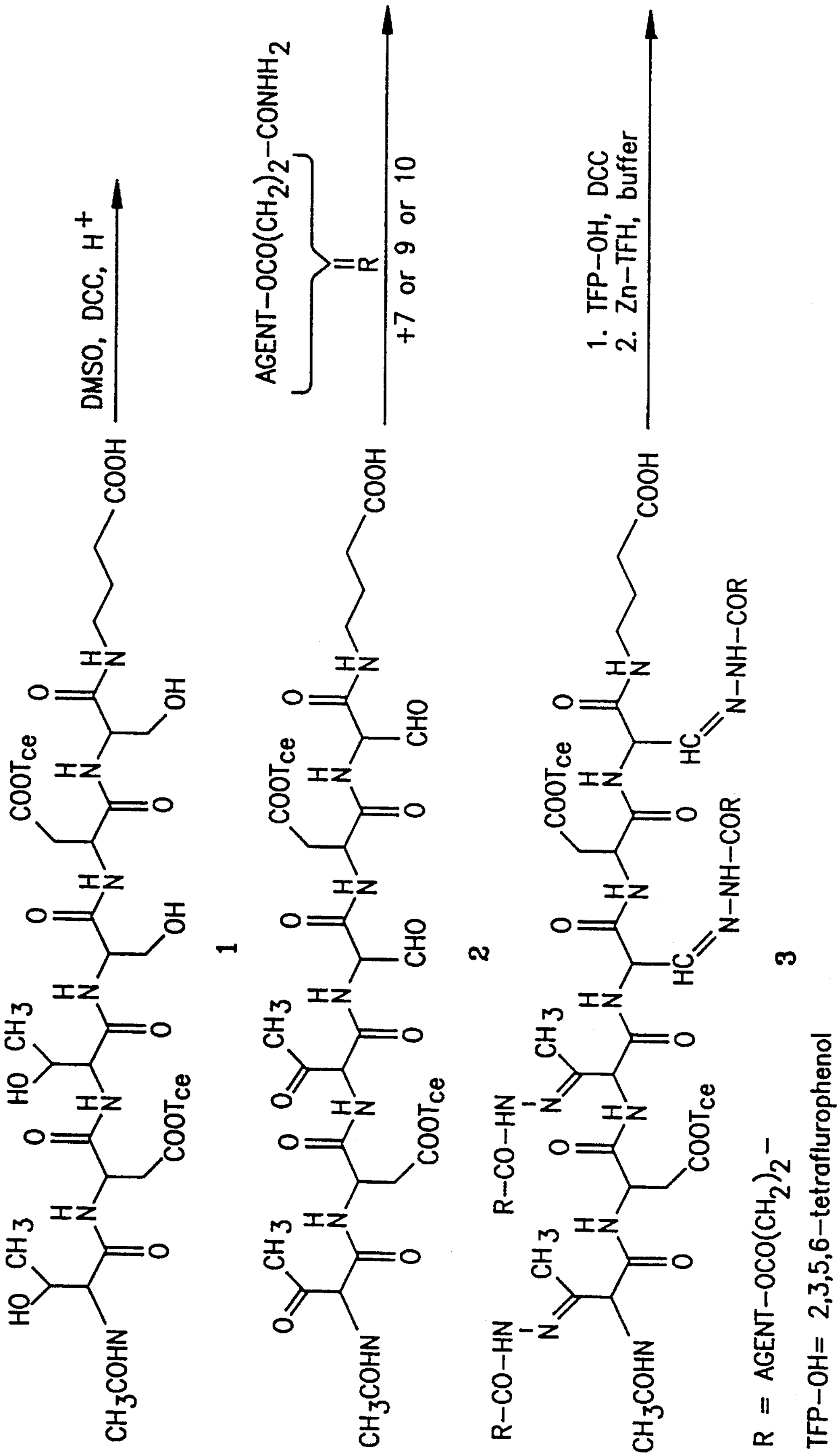
FIG. 2 is a flow chart representing a procedure for the synthesis of a polymeric carrier with attached therapeutic agents and the conjugation of the polymeric carrier to an antibody.
Figure 2B:
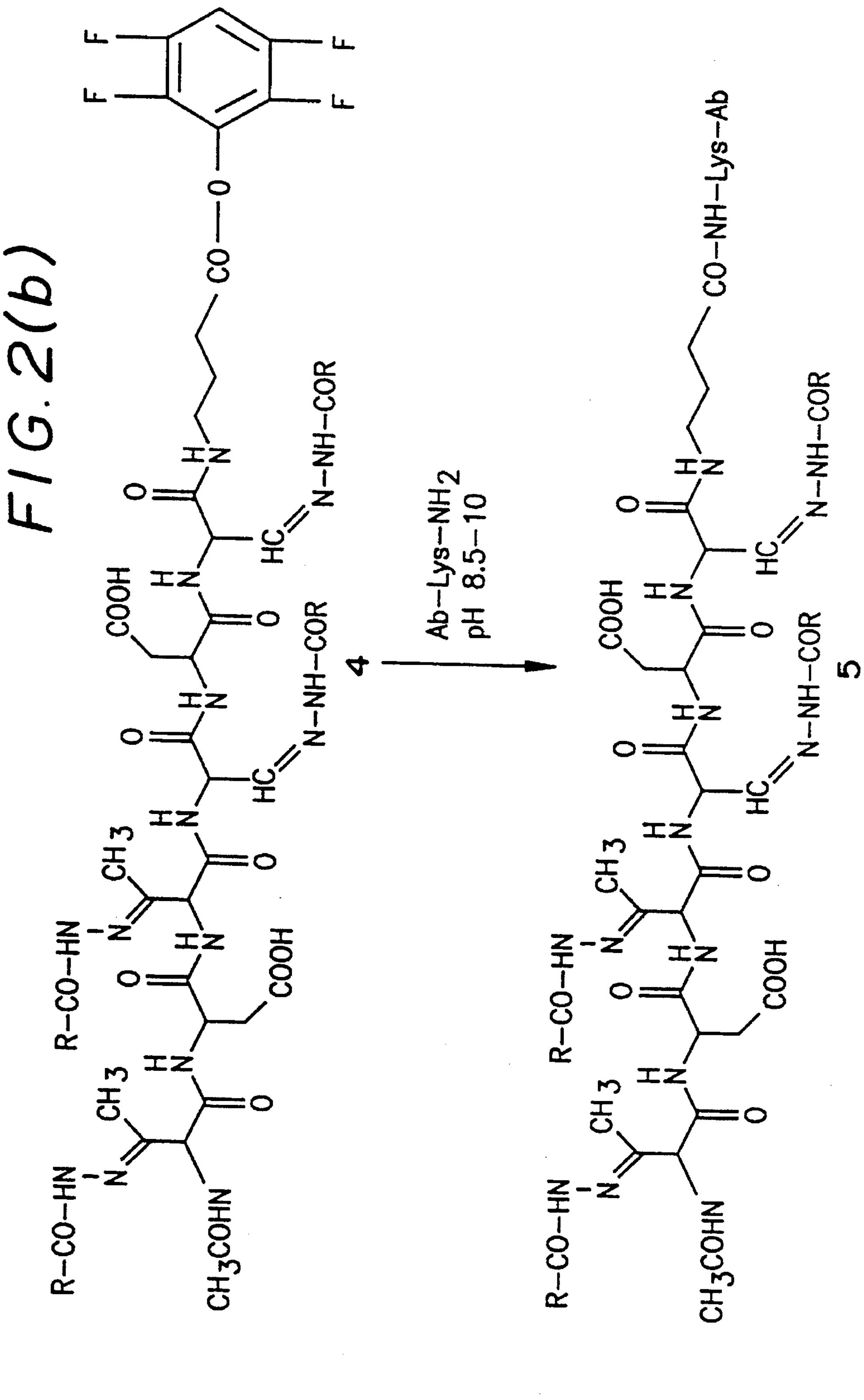

This example first involves the synthesis of peptide 1 [SEQ ID NO.: 1], N-Acetyl-L-seryl-L-aspartyl(β-Otce)-L-seryl-L-threonyl-L-aspartyl-(β-Otce)-L-threronyl-γ-aminobutyric acid. This is followed by the oxidation of the hydroxyl amino acid side chain groups to carbonyl groups. These carbonyl groups are then condensed with the hydrazide groups on the agents. Next, there is formation of the active ester on the C-terminal of the peptide. This enables the peptide or polymeric carrier with attached agents to conjugate with the antibody. The general procedure for the synthesis of a polymeric carrier with attached agents and the conjugation of the polymeric carrier to an antibody is illustrated in FIG. 1. FIG. 2 illustrates a specific polymeric carrier synthesis and a specific conjugation procedure.

The above compounds are synthesized as C-terminal carboxylates using PAM resin attached to the first C-terminal amino acid (J. M. Stewart and J. Young, "Solid phase peptide synthesis", Pierce Chemical Company, Rockford, Ill., 1984)) on an Applied Biosystems 430 A synthesizer using its specific protocols with N-methylpyrrolidone as a coupling solvent (User's manual. Model 430A synthesizer. Applied Biosystems, Inc., Foster City, Calif.)).

The preferred protecting groups are Ser (O-benzyl), Thr (O-benzyl), Glu(O-t-butyl), Glu(O-benzyl), Asp(O-t-butyl) and Tyr(Br-Cbz) (G. Barany and R. B. Merrifield, "The Peptides. Analysis, Synthesis and Biology" E. Gross and J. Meinhofer, Editors, Academic Press, New York, pages 1–284 (1980)). The other preferred protecting group for glutamic and aspartic acids (and other carboxyl bearing side chains) is the trichloroethyl ester trichloroethoxycarbonyl for tyrosine (Tce). The presence of this protecting group on the carboxyl of Asp and Glu residues offer protection through the sequence of derivatization of the side chain, attachment of the agents and the final activation of the terminal carboxyl group for conjugation to the targeting molecule. After the activation, the trichloroethyl group(s) can be removed by the using Zn-HOAc or Zn-THF-phosphate buffer (R. B. Woodward, K. Heusler, J. Gosteli, P. Naegeli, W. Oppolzer, R. Ramage, S. Ranganathan and H. Vorbruggen, J. Amer. Chem. Soc., 88, 852 (1989) and M. F. Sommelhack and G. E. Heinsohn, J. Amer. Chem Soc., 94, 5139 (1972)). After first deblocking by trifluoroacetic acid, the N-terminal residue is acetylated using acetic anhydride and finally cleaved from this resin using HF (See FIG. 1).

The cleavage of peptides from the resin are accomplished using the low-high HF cleavage procedure of Tam and Merrifield (J. P. Tam, W. F. Heath and R. B. Merrifield, "$S_N2$ deprotection of synthetic peptides with low concentration of HF in dimethyl sulfide: evidence and application in peptide synthesis." J. Amer. Chem. Soc., 105, 6442 (1983)) (method A) or in 10:1:1:2 (by volume) of HF:anisole:dimethylsulfide:p-thiocresol for 1 hour at 5° to 0° C. After cleavage, the organic scavengers are extracted from the resin 3 times with ether and the peptides extracted twice with 5 mL volume of 20–40% $HOAc/H_2O$. After lyophilization, the peptides are purified on a semi-preparative Vydec LC4 reversed phase column using a gradient of 100% $H_2O$—0.1% TFA to 40% $H_2O$—0.1% TFA+60% $CH_3CN$—0.1% TFA. They are analyzed for correct amino acid composition and molecular weight by FAB mass spectrometry (T. D. Lee, "Methods of Protein Microcharacterization" J. E. Shively, editor. The Humana Press, Clifton, N.J., p. 403 (1986).

It is necessary to prepare the corresponding C-14 labeled peptides at the N-terminal residue acetyl for the purpose of determining the stoichiometry of attachment of peptides and modified peptides containing therapeutic molecules. The N-terminal residue after the first deblocking of the N-terminal Boc group is acetylated using labeled acetic anhydride. As an example, 10 mg of the peptide is N-acetylated with C-14-acetic anhydride (1 mCi, 11.3 mCi/mmol) which is added and shaken for 2.5 hours with the resin. A 5-fold molar excess of diisopropylethylamine was added and N-acetylation was continued for 30 minutes. Peptide resin sealed in 1 inch square polypropylene bags was washed several times with 4 mL/bag of methylene chloride, 5% diisopropylethylamine/methylene chloride and finally with 10% cold acetic anhydride/methylene chloride to complete the acetylation. Excess labelled anhydride was washed from the resin by consecutive rinses of methylene chloride, dimethyl formamide, isopropanol, methylene chloride, methanol and the resin was dried overnight prior to deblocking by the procedures described above.

To avoid the potential proteolytic degradation of the peptide or polymeric carrier attached to the targeting molecules while in the serum, the N-terminal residue or all the residues are in the D-configuration. The change in the configuration of the peptide backbone will not alter the rate of the release of the therapeutic molecules attached to the side chain. However, this change may diminish the immunogenicity of the peptide backbone of these carriers.

The next step involves Moffatt oxidation of peptide 1 to the corresponding carbonyl compound 2. The oxidation of the peptide is carried out using DMSO, DCC, pyridine trifluoroacetate, and benzene or toluene. Moffatt oxidation is preferred for compound 2 since the procedure does not result in over oxidation of the hydroxyl compound. (For general methods see, A. F. Cook and J. G. Moffatt, J. Amer. Chem. Soc., 89, 2697 (1967) and K. E. Pfitzner and J. G. Moffatt, J. Amer. Chem Soc., 87, 5661 (1965)).

The next step is preparation (modification) of therapeutic molecules by changing their alcohol groups to hydrazides and then condensing them with modified peptides. The therapeutic molecules of interest are Verrucarin A and Roridin A which belong to the trichothecene group of antibiotics (B. B. Jarvis and A. Acierto in "Trichothecene Mycotoxicosis: Pathyophysiological Effects" Vol. 1. V. R. Beasley, Editor, CRC Press, Boca Raton, Fla., 1989. pp. 73–105). These compounds with broad spectrum biological activities are the most potent synthesis inhibitors containing C, H and O. They exert their inhibition by interacting with the EF2 on the ribosomes (C. S. McLaughlin, M. H. Vaughen, I. M. Campbell, I. M. Wei and B. S. Hansen, "Mycotoxins in Human and Animal Health", J. V. Rodericks, Editor. Pathotox Publishers, 1977, pp 263–273). The structures of these compounds are shown below. Verrucarin A (6) and Roridin A (8) were converted to the corresponding succinyl hydrazide derivatives (7 from 6,9 and 10 from 8) according to published procedures (R. O. Kollah, "The Chemistry and Biology of Macrocyclic Trichothecenes", Ph.D. Thesis, University of Maryland, 1989, M. Zeng, "Studies in Chemical and Biological Structures of Macrocyclic Trichothecenes", Ph.D. Thesis, University of Maryland, 1989; V. M. Vrudhula, T. M. Comezoglu and A. Srinivasan, Abstract No. MEDI 50, ACS National Meeting, Boston, Mass., April 1990).

A similar strategy can be used to convert other molecules of therapeutic intrest containing alcohol function to hydrazide (after incorporating a succinyl moiety) for attachment to the defined polymer 2. In a similar manner, molecules of therapeutic interest containing a carboxylic acid function can be attached to the defined polymer via the formation of a hydrazide.

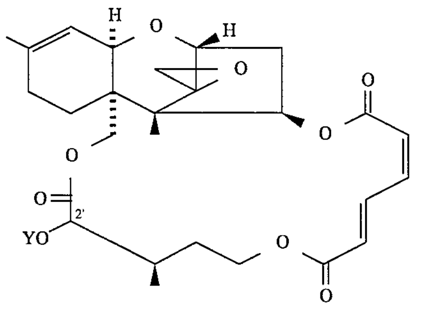

Y = H Verrucarin A 6
Y = CO—$(CH_2)_2$—$CONHNH_2$ 7
Verrucarin A—O-succinyl hydrazide
Compound 6 → Compound 7

Compound 8 → Compound 9, Compound 10

In FIG. 2, Macrocycle-O—CO—$(CH_2)_2$=R

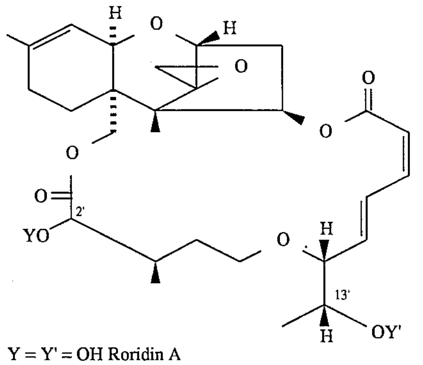

Y = Y' = OH Roridin A
Y = CO—$(CH_2)_2$—$CONHNH_2$; R' = H 9
(Roridin A-2'-O-succinyl hydrazide)
Y = H; Y' = CO—$(CH_2)_2$—$CONHNH_2$ 10
(Roridin A-13'-O-succinyl hydrazide)

The next procedure is preparation of hydrazone 3 from compound 2 and Verrucarin A hydrazide 7. To a solution of the peptide (1 mmol) in isopropanol 5 mmol of Verrucarin A hydrazide (7; 10 mmol) is added and the solution is allowed to stand at room temperatures for several hours. The formation of hydrazone is followed chromatographically and is isolated either by crystallization or by C-18 column chromatography. The product is characterized by NMR and FAB mass spectrometry.

The hydrazone derived from peptide 4 and Roridin A derivatives 9 and 10 are prepared in a similar manner.

Figure 3:
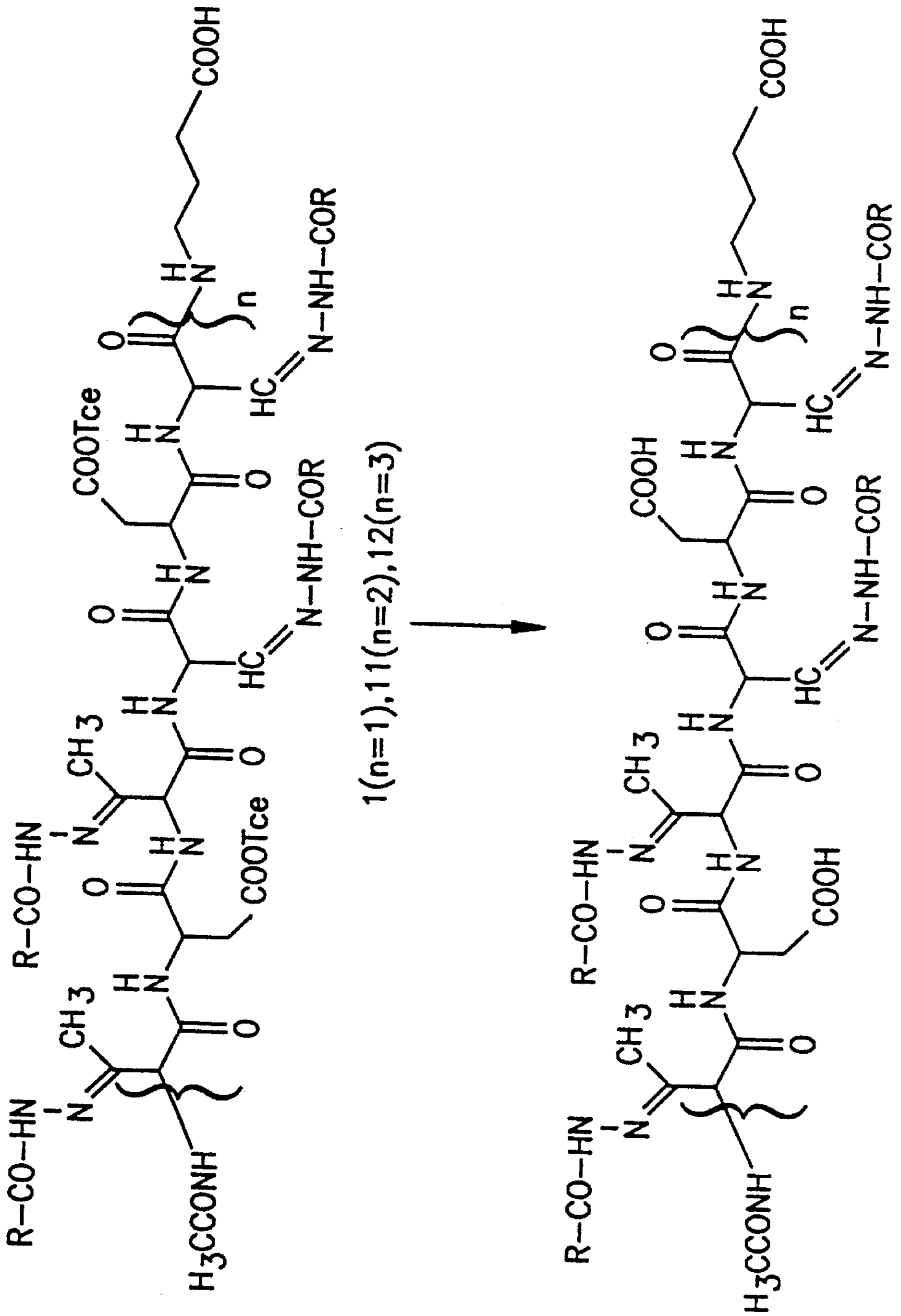
FIG. 3 illustrates the removal of protecting groups from amino acid side chains of a polymeric carrier.

The next synthesis is the preparation of active ester 4 of peptide 3 (See FIG. 3). To a solution of the peptide 3 in DMF, from the above reaction, 3 equivalents of 2,3,5,6-tetrafluorophenol and 3 equivalents of DCC are added and the solution is stirred at room temperature for 10–12 hours. The precipitated dicyclohexylurea is removed by filtration and the residue is chromatographed to isolate the product.

The product is dissolved in a phosphate buffer containing 10% tetrahydrofuran and the trichloroethyl groups are removed according to the procedure of M. F. Sommelhack and G. E. Heinsohn (J. Amer. Chem. Soc., 94, 5139 (1972)) to yield the peptide or polymeric carrier 4, containing the therapeutic molecules and an active ester for attachment to the targeting molecule.

The last step is the conjugation of the active ester 4 to the NR-LU-10 to give the conjugate 5. The active ester is condensed with NR-LU-10 murine monoclonal antibody, which recognizes a pancarcinoma antigen. Other proteins or fragments may be substituted for the NR-LU-10 antibody. To a solution of the antibody at pH 9–9.5, a solution of the active ester in 250mM bicarbonate buffer at pH 9.3 is added and gently agitated to mix and incubated at room temperature for 30 minutes to allow conjugation of the peptide carrier to the antibody. The conjugate is purified in a column containing an anion exchanger DEAE-sephadex or QAE-sephadex. All of the above reactions are shown in FIG. 2.

In a similar manner, conjugates are prepared from longer chain peptides, N-Acetyl-[L-seryl-L-aspartyl(β-Otce)-L-seryl-L-threonyl-L-aspartyl-(β -Otce)-L-threonyl]$_2$-γ-aminobutyric acid, peptide 11 and N-Acetyl-L-seryl-L-aspartyl(β-Otce)-L-seryl-L-threonyl-L-aspartyl β-Otce)L-threonyl-γ-aminobutyric acid, peptide 12.

General procedure for the evaluation of stability of hydrazones follows. Prior to the evaluation of conjugates the hydrazones derived from peptides 1, 11, and 12 are converted to the free acids 13–15 (see FIG. 3). For the experiments in human serum stability, the hydrazone under investigation is incubated in fresh human serum at 37° C. at a concentration of 1 mg/mL. Aliquots (100 μL) at different time points (2–150 hours) are diluted with equal volumes of acetonitrile. The suspension is centrifuged and the centrifugate is analyzed by HPLC for the presence of the therapeutic drug released. In a similar manner, the compounds are tested for their stability at pH 5.6.

EXAMPLE 2

This example covers the attachment of bifunctional chelate ligands to the defined peptide or polymeric conjugation of the carrier to the antibody followed by radiolabeling.

Figure 4A:
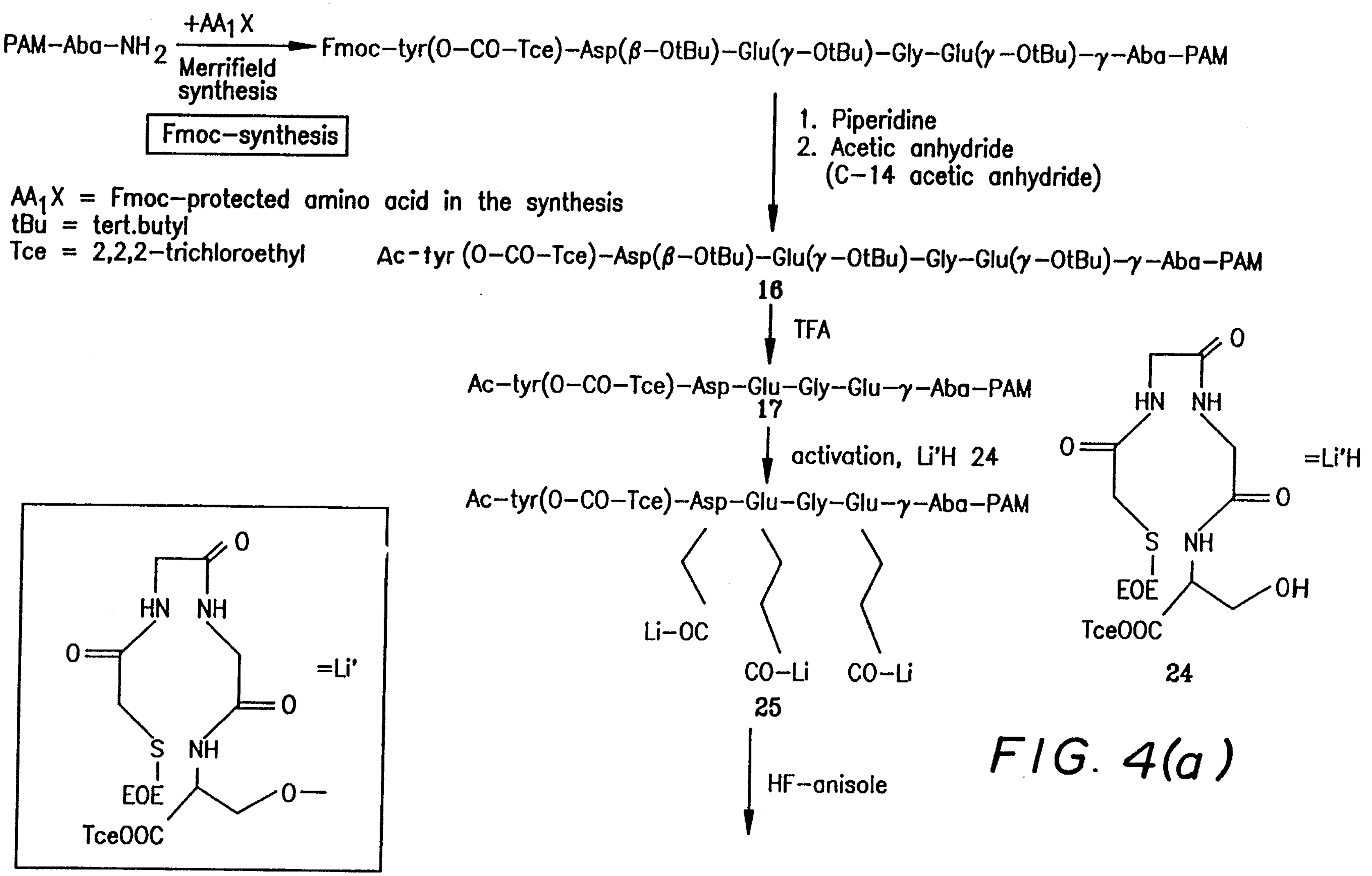
FIGS. 4 [SEQ ID NOS.: 9–14] and 6 are flow charts representing procedures for the synthesis of polymeric carriers with attached chelating agents and the conjugation of the polymeric carriers to antibodies.
Figure 4B:
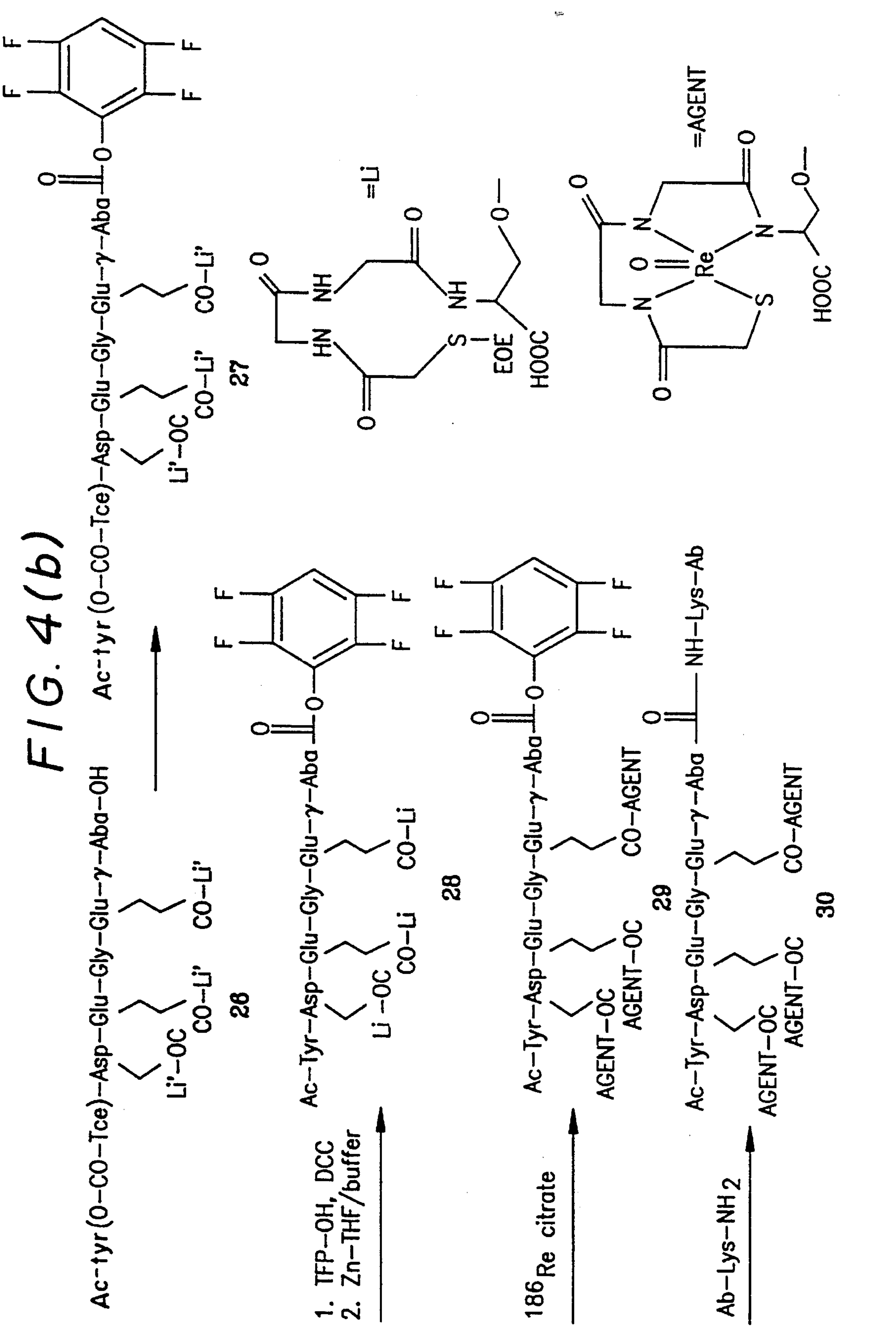

The procedures in this example are the synthesis of [SEQ ID NO.: 2] N-Acetyl-L-tyrosyl (O—CO—$CH_2$—$CCl_3$)-L-Asp(β-OtBu)-Glu(γ-OtBu)Gly-Glu(γ-OtBu)-γ-Aba-PAM resin 16, the removal of protecting groups from the carboxyl groups in Asp and glutamyl residues using trifluoroacetic acid to synthesize, peptide 17, the condensation of bifunctional chelate, S-ethoxyethylmercapto-acetylglycylglycylserinetrichloroethyl ester 24 to give 25, the cleavage of this peptide from the resin to give 26, the activation of the terminal carboxylic acid to give 27, the deprotection (to 28), and the radiolabeling to give the chelate 29, followed by conjugation to the antibody to yield the conjugate 30 (see FIG. 4).

The requisite peptide, N-Acetyl-L-tyrosyl (O—CO—$CH_2$—$CCl_3$)-L-Asp(β-OtBu)-Glu(γ-OtBu)-Gly-Glu(γ-OtBu)-γ-Aba-PAMresin 16, is synthesized using solid phase methodology of Merrifield (G. Barany and R. B. Merrifed, "The Peptides. Analysis, Synthesis and Biology" E. Gross and J. Meinhofer, Editors, Academic Press, New York, pages 1–284 (1980)). The protecting group in each step is 9-flourenylmethoxycarbonyl (Fmoc) rather than the N-tBoc group used in the synthesis of 1. This methodology conserves the protecting group of the Glu and Asp (and other amino acid residues bearing a carboxyl side chain). Removal of the Fmoc protecting group in each successive step is accomplished by using aqueous piperdine. Acetylation is accomplished according to the procedure described earlier.

Preparation of C-14 labeled peptides at the N-terminal residue acetyl. It is necessary to prepare the corresponding C-14 labeled peptides for the purpose of determining the stoichiometry of attachment of peptides and modified peptides containing therapeutic molecules. The N-terminal residue after the first deblocking of the N-terminal Fmoc group is acetylated using labeled acetic anhydride. As an example, 10 mg of the peptide is N-acetylated with C-14 acetic anhydride (1 mCi, 11.3 mCi/mmol) which is added and shaken for 2.5 hours with the resin. A 5-fold molar excess of diisopropylethylamine is added and N-acetylation was continued for 30 minutes. Peptide resin sealed in 1 inch square polypropylene bags was washed several times with 4 mL/bag of methylene chloride, 5% diisopropylethylamine/methylene chloride and finally with 10% cold acetic anhydride/methylene chloride to complete the acetylation. Excess labelled anhydride is washed from the resin by consecutive rinses of methylene chloride, dimethyl formamide, isopropanol, methylene chloride, methanol and the resin was dried overnight prior to removal of the t-Boc protecting groups.

To avoid the potential proteolytic degradation of the peptide carrier attached to the biological macromolecules while in the serum, the N-terminal residue or all the residues are in the D-configuration. The change in the configuration of the peptide back bone will not alter the rate of the release of the therapeutic molecules attached to the side chain. This change may also diminish the immunogenicity of the peptide backbone of these carriers.

The synthesis of [SEQ ID NO.: 3] N-Acetyl-L-Tyr-L-Asp-Glu-Gly-Glu-γ-Aba PAM resin 17. The peptide still attached to the resin is deblocked using trifluoroacetic acid (conversion of tbutyl esters of glu and asp residues) to —COOH according to the general procedure (G. Barany and R. B. Merrifield, "The Peptides. Analysis, Synthesis and Biology" E. Gross and J. Meinhofer, Editors, Academic Press, New York, pages 1–284 (1980)).

The synthesis of S-ethoxyethylmercaptoacetylglycylglycylserinetrichloroethyl ester 24 (see FIG. 5) involves first the synthesis of N-t-Boc-Serine-O-benzyltrichloroethyl ester 18. To a solution of N-t-Boc-serine-O-benzyl ether (5 mmol) in methylene chloride containing 5 mmol of triethylamine, 5 mmol of N, N-dicyclohexylcarbodiimide was added and the solution was stirred at room temperature overnight. The precipitated dicyclohexylurea was filtered and the filtrate was washed with 1% HCl and water. The organic layer was dried over anhydrous $Na_2SO_4$, and evaporated to give the trichloroethyl ester, which was purified over a silica gel column.

Serine trichloroethyl ester trifluoroacetate 19 is prepared in the following manner. A solution of 4 mmol of the above compound 18, in 50 mL of glacial acetic acid containing 200 mg of palladium on charcoal was hydrogenated at 60 psi in a Paar apparatus for 10–12 hours. The catalyst was removed by filtration over celite and the solvent was removed in vacuo to give N-t-Boc serine trichloroethyl ester, an oil, which was dried overnight and used without further purification. The oil was stirred with 10 mL 50% trifluoroacetic acid-$CH_2Cl_2$ for 3 hours at room temperature to remove the Boc group. The mixture was evaporated to dryness, coevaporated several times with methylene chloride and dried to give 19. The compound was homogeneous by TLC and was used in the next step without further purification.

S-(1-ethoxylethyl) mercaptoacetic acid 20 is prepared according to the following. A solution of mercaptoacetic acid (17.4 mL, 250 mmol) in 125 mL of dichloromethane containing p-toluenesulfonic acid monohydrate (0.24 g, 1.26 mmol) was cooled to −18° to −25° C. with stirring. Ethyl vinyl ether (23.9 mL, 250 mmol) in 125 mL of dichloromethane was added dropwise to the cold solution over a period of 90 minutes. The stirring was continued for an additional 30 minutes with the temperature maintained in the −18° to −25° C. range. Then 200 mL of pH7 phosphate buffer was added, and the reaction mixture was allowed to warm with stirring for 10 to 15 minutes The mixture was then poured into a flask containing 900 mL of theyl acetate and 200 mL of water. Layers were separated and the aqueous portion extracted twice with ethyl acetate. The organic layers were combined, washed with brine and dried ($MgSO_4$). Removal of the solvent left 31.4 g of S-(1-ethoxyethyl) mercaptoacetic acid 20 as a colorless oil (77% yield): $^1H$ NMR ($CDCl_3$) 1.15 (t, J=7.0Hz, 3H), 1.52 (d, J=6.4Hz, 3H), 3.36 (s, 2H), 3.60 (m, 2H), 4.84 (q, J=6.4Hz, 1H), 11.65 (s, 1H). The material was used without further purification.

Succinimidyl S-(1-ethoxyethyl) mercaptoacetate 21 is prepared according to the following procedure. A solution of S-(1-ethoxyethyl) mercaptoacetic acid (5.76 g, 35.1 mmol) and N-hydroxysuccinimide (4.85 g, 42.1 mmol) was prepared in 100 mL of anhydrous THF. To this was added a solution of 1,3-dicyclohexylcarbodiimide (8.70 g, 42.1 mmol) in 65 mL of anhydrous THF. The mixture was stirred at room temperature for 2 hours or until TLC analysis indicated complete formation of the succinimidyl ester. The mixture was then filtered, and the filtrate was concentrated in vacuo to a viscous residue. The residue was dissolved in ethyl acetate, washed with water, brine, and dried ($MgSO_4$). Removal of the solvent left the crude succinimidyl ester as an oil, which was further purified by flash chromatography on silica gel, using ethyl acetate-hexanes as the column eluent, to give 5.1 g of S-(1-ethoxyethyl) mercaptoacetic acid succinimidyl ester as a colorless oil (56% yield): $^1H$ NMR ($CDCl_3$) 1.21 (t, J=7.0Hz, 3H), 1.58 (d, J=6.4Hz, 3H), 2.83 (s, 4H), 3.60 (m, 4H), 4.88 (q, J=6.4Hz, 1H).

The synthesis of 22 is as follows. Solid $NaHCO_3$ (1.09 g, 13.0 mmol) was added to a solution of glycylglycine (1.22 g, 9.3 mmol) in 10 mL of water. After gas evolution ceased, a solution of (2.66 g, 10.2 mmol) in 12 mL of $CH_3CN$ was added to the reaction mixture. The mixture was stirred at room temperature for 22 h, then evaporated in vacuo. The residue was purified by flash chromatography on silica gel (85:10:5 $CH_3CN$:$H_2O$:HOAc) to yield 2.2 g (86%) of 22 as a viscous oil. $^1H$ NMR (DMSO) 8.26 (t, 1H), 8.08 (t, 1H), 4.80 (q, 1H), 3.73 (m, 4H), 3.52 (m, 2H), 3.24 (s, 2H), 1.43 (d, 3H), 1.10 (t, 3H).

The following are details on the synthesis of 23. 1,3 Dicyclohexylcarbodiimide (0.66 g, 3.2 mmol) was added to a stirring solution of 22 (0.81 g, 2.9 mmol) and N-hydroxysuccinimide (0.37 g, 3.2 mmol) in 10 mL of CH3CN. After stirring for 2 h, the mixture was filtered and the filtrate was evaporated in vacuo. The residue was purified by flash chromatography on silica gel (96:4 EtOAc:HOAc) to yield 0.80 g (73%) of 23 as a viscous oil. $^1H$ NMR (DMSO) 8.54 (t, 1H), 8.29 (t, 1H), 4.80 (q, 1H), 4.27 (d, 2H), 3.78 (d, 2H), 3.53 (m, 2H), 3.24 (s, 2H), 2.81 (s, 4H), 1.43 (d, 3H), 1.09 (t, 3H).

Figure 5:
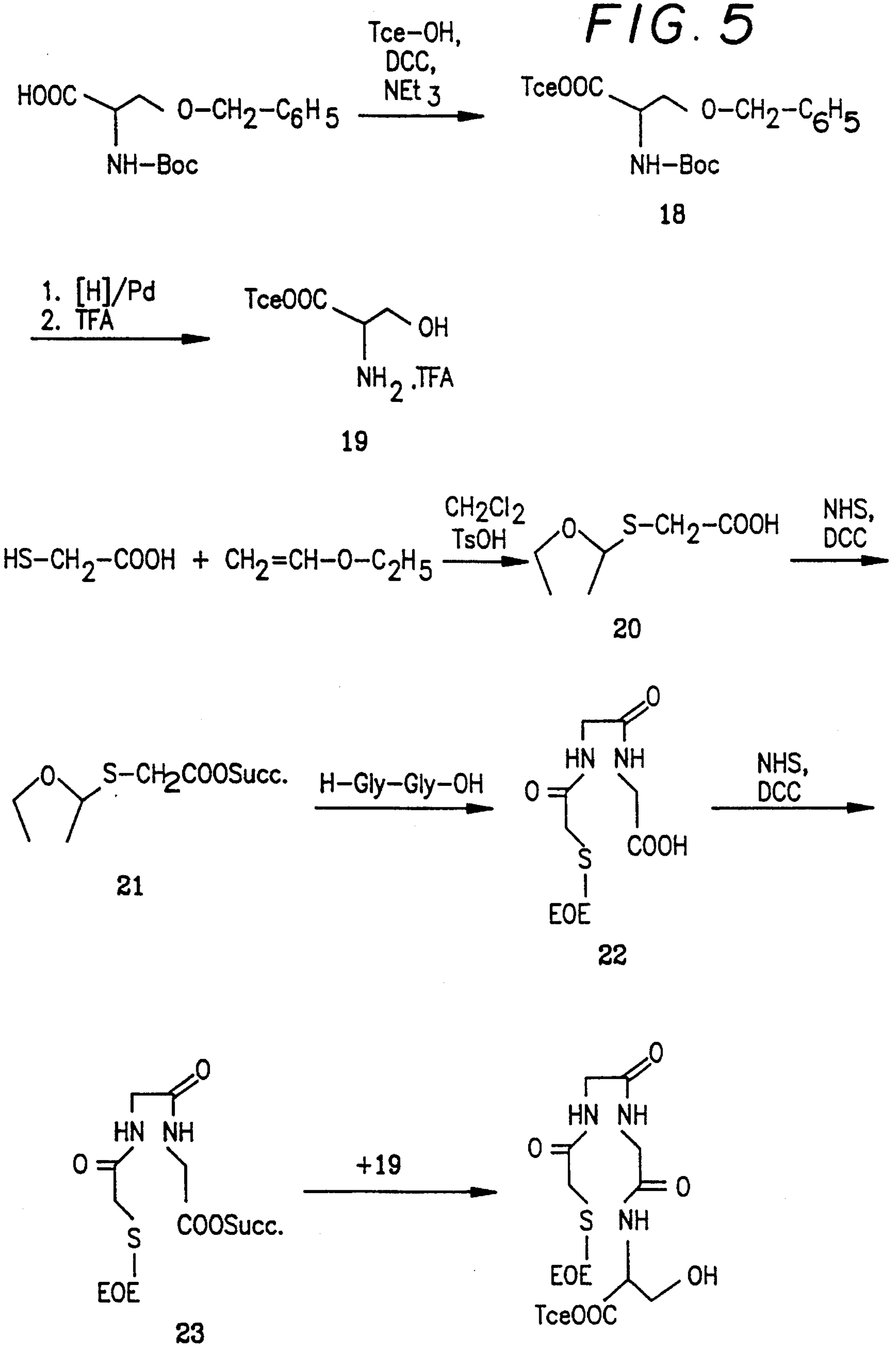
FIG. 5 [SEQ ID NO. 15] is a flow chart representing a procedure for the synthesis of a chelating agent.

The synthesis of S-ethoxyethylmercaptoacetylglycyl glycylserinetrichloroethyl ester 24 is prepared in the following manner (see FIG. 5). Triethyl-amine (2 mmol) was added to a solution of 19 (1.7 mmol) and 23 (1.7 mmol) is 5 mL of anhydrous dimethylformamide. After stirring for 2.5 hours at room temperature the mixture was evaporated in vacuo. The resulting residue was taken up in ethyl acetate (20 mL) and washed with water, saturated sodium chloride and dried over sodium sulfate, filtered and evaporated. The residue was purified over a C-18 column to give pure 24, which was used in the condensation.

The condensation of 24 with the -COOH residues of Glu and Asp in 17 occurs in the following manner. Solid cleavage of peptides from the resin is accomplished using the low-high HF cleavage procedure of Tam and Merrifield (J. P. Tam, W. F. Heath and R. B. Merrifield, "$SN_2$ deprotection of synthetic peptides with low concentration of HJ in dimethyl sulfide: evidence and application in peptide synthesis." J. Amer. Chem. Soc., 105, 6442 (1983)) (Method A) or in 10:1:1:2 (by volume) of HF:anisole: dimethylsulfide:p-thiocresol for 1 hour at 5°–0° C. After cleavage, the organic scavengers are extracted from the resin 3 times with ether and the peptides extracted twice with 5 mL volume of 20–40% HOAc/$H_2O$. After lyophilization, the peptides are purified on a semi-preparative Vydec LC4 reversed phase column using a gradient of 100% $H_2O$—0.1% TFA to 40% $H_2O$—0.1% TFA+60% $CH_3CN$—0.1% TFA. They are analyzed for correct amino acid composition and molecular weight by FAB mass spectrometry (Ref. T. D. Lee, "Methods of Protein Microcharacterization" J. E. Shively, editor. The Humana Press, Clifton, N.J., p. 403 (1986)).

The following is the preparation of the active ester 27 of 26. To a solution of the peptide 26 in DMF, from the above reaction, 3 equivalents of 2,3,5,6tetrafluorophenol and 3 equivalents of DCC are added and the solution is stirred at room temperature for 10–12 hours. The precipitated dicyclohexylurea is removed by -filtration and the residue is chromatographed to isolate the product, 27.

The product 27 is dissolved in a phosphate buffer containing 10% tetrahydrofuran and the trichloroethyl groups are removed according to the procedure of M. F. Sommelhack and G. E. Heinsohn (J. Amer. Chem Soc., 94, 5139 filtration and the residue is chromatographed to isolate the product, 27.

The product 27 is dissolved in a phosphate buffer containing 10% tetrahydrofuran and the trichloroethyl groups are removed according to the procedure of M. F. Sommelhack and G. E. Heinsohn (J. Amer. Chem Soc., 94, 5139 (197Z)) to yield the peptide carrier 28, containing the chelator capable of forming metabolically stable complexes with radionuclides and an active ester for attachment to the targeting molecule.

The following is the radiolabeling procedure with $^{186}Re$. The peptide containing the chelator radiolabeled with $^{186}Re$ according to the following procedure. Sodium perrhenate produced from a W/Re generator is combined with citric acid (a preferred complexing agent for $^{186}Re$), a reducing agent (usually $SnCl_2$). The resulting $^{186}Re$-citrate exchange complex is heated with the chelating compound 28 at 75°–100° C. for 10–15 minutes and then transferred to a 0° C. ice bath for a few minutes to obtain the peptide 29 containing $^{186}Re$-complexes on the side chain.

The above solution containing the chelate is removed from the ice bath, 2.0 mL of 250 mM sodium bicarbonate buffer (pH 9–10) is added and the vial is agitated to mix. Immediately, the antibody (whole or fragments) is added and incubated at room temperature for 10–15 minutes to complete the conjugation to the antibody. The conjugate so produced is purified using an anion exchange column (DEAE-sephadex or QAE-sephadex) prepared under aseptic conditions to yield 30.

Figure 6:
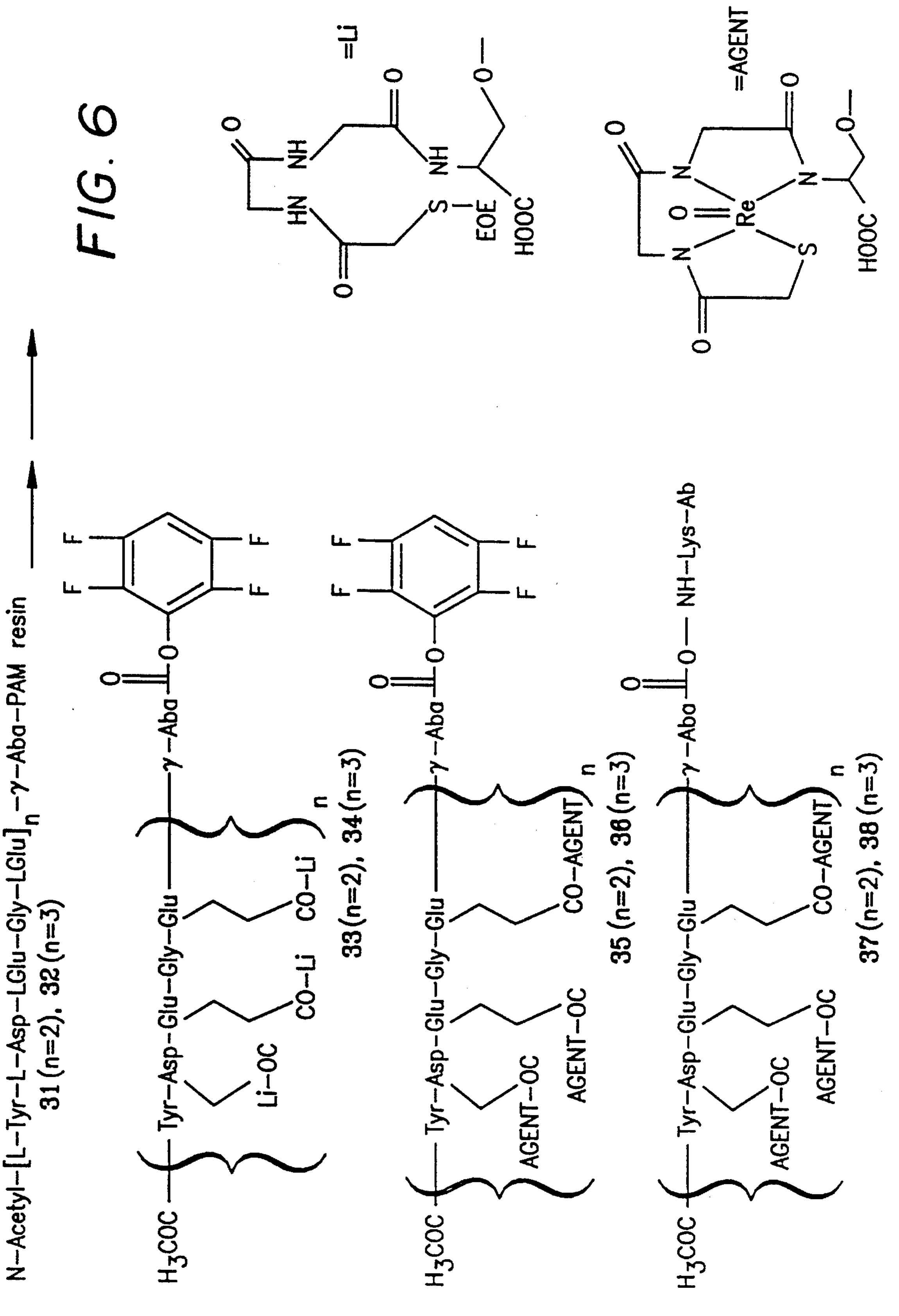

In a similar approach, peptides 31 and 32 are synthesized by solid phase procedure and the antibody conjugates 37 and 38 prepared. The intermediates in the case of these oligomer syntheses are shown in FIG. 6.

The invention now being fully described, it will be apparent to one of ordinary skill in the art that many changes and modifications can be made without departing from the spirit or scope of the invention.

We claim:

1. A polymeric carrier comprising a series of α-amino acids which are the same or different and which contain side chains to which agents covalently join through cleavable linkers after chemical modification of the side chains represented by the formula:

$$\begin{array}{l}(PG)_r\text{—}(AA)_n\text{—}SG\text{+}CG)_s \\ \qquad\qquad\quad | \\ \qquad\quad (AGENT)_m\end{array}$$

wherein

PG is a N-terminal protecting group;

AA is an α-amino acid selected from the group consisting of lysine, arginine, histidine, cysteine, tyrosine, tyrosine-O—$SO_3$—, serine and threonine, aspartic acid, glutamic acid, asparagine and glutamine, wherein $(AA)_n$ does not comprise (1) any two adjacent amino acids which are the same, (2) any two adjacent amino acids selected from the group consisting of aspartic acid, glutamic acid, asparagine and glutamine;

SG is a spacer group which prevents stearic hindrance by agents attached to the polymeric carrier and which promotes attachment of the polymeric carrier to a targeting molecule;

CG is a conjugation group which provides for the attachment of the polymeric carrier to a targeting molecule;

AGENT is a diagnostic or therapeutic agent, or a chelating agent which binds a diagnostic or therapeutic metal radionuclide;

n is from 2 to 18;

m is from 2 to 18;

r is 0 or 1; and s is 0 or 1.

2. The polymeric carrier of claim 1 wherein the N-terminal protecting group, PG, is selected from the group consisting of acetyl, proprionyl, phenacyl sulfonyl and substituted phenacylsulfonyl.

3. The polymeric carrier of claim 1 wherein the spacer group, SG, is selected from the group consisting of aminocaproic acid, aminopentanoic acid, γ-aminobutyric acid, β-alanine and glycine.

4. The polymeric carrier of claim 1, wherein the conjugation group, CG, is selected from the group consisting of active esters, thioisocyanotes, amines, hydrazines, maleimides or other Michaels-type acceptors, thiols and activated halides.

5. The polymeric carrier of claim 1, wherein the α-amino acids are all in the L configuration.

6. The polymeric carrier of claim 1, wherein the α-amino acids are all in the D configuration.

7. The polymeric carrier of claim 1, wherein the α-amino acids comprise a combination of L and D amino acids.

8. The polymeric carrier of claim 1, wherein the α-amino acids are covalently joined to agents through hydrazone linkages, disulfide linkages, ester linkages, and any combinations thereof.

9. The polymeric carrier of claim 1, which is covalently attached to a targeting molecule.

10. The polymeric carrier of claim 9 wherein said targeting molecule is an antibody or fragment thereof, hormone, enzyme or biological response modifier.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..3
        ( D ) OTHER INFORMATION: /note="Peptides 1, 2 & 3 wherein Xaa =N- Acetyl-L"

( i x ) FEATURE:
        ( A ) NAME/KEY: Peptide
        ( B ) LOCATION: 5
        ( D ) OTHER INFORMATION: /note="Peptide 5 wherein Xaa =L"

( i x ) FEATURE:
        ( A ) NAME/KEY: Peptide
        ( B ) LOCATION: 7
        ( D ) OTHER INFORMATION: /note="Peptide 7 wherein Xaa = beta-Otce"

( i x ) FEATURE:
        ( A ) NAME/KEY: Peptide
        ( B ) LOCATION: 8
        ( D ) OTHER INFORMATION: /note="Peptide 8 wherein Xaa =L."

( i x ) FEATURE:
        ( A ) NAME/KEY: Peptide
        ( B ) LOCATION: 10
        ( D ) OTHER INFORMATION: /note="Peptide 10 wherein Xaa = L."

( i x ) FEATURE:
        ( A ) NAME/KEY: Peptide
        ( B ) LOCATION: 12
        ( D ) OTHER INFORMATION: /note="Peptide 12 wherein Xaa = L."

( i x ) FEATURE:
        ( A ) NAME/KEY: Peptide
        ( B ) LOCATION: 14
        ( D ) OTHER INFORMATION: /note="Peptide 14 wherein Xaa = beta- Otce."

( i x ) FEATURE:
        ( A ) NAME/KEY: Peptide
        ( B ) LOCATION: 15
        ( D ) OTHER INFORMATION: /note="Peptide 15 wherein Xaa = L."

( i x ) FEATURE:
        ( A ) NAME/KEY: Peptide
        ( B ) LOCATION: 17
        ( D ) OTHER INFORMATION: /note="Peptide 17 wherein Xaa = gamma."

( i x ) FEATURE:
        ( A ) NAME/KEY: Peptide
        ( B ) LOCATION: 18
        ( D ) OTHER INFORMATION: /note="Peptide 18 wherein Xaa = aminobutyric acid."

( x i ) SEQUENCE DESCRIPTION: SEQ ID NO:1:

```
Xaa  Xaa  Xaa  Ser  Xaa  Asp  Xaa  Xaa  Ser  Xaa  Thr  Xaa  Asp  Xaa  Xaa  Thr
 1                 5                           10                          15
```

Xaa Xaa ( 2 ) INFORMATION FOR SEQ ID NO:2:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..3
( D ) OTHER INFORMATION: /note="Peptides 1-3 wherein Xaa = N-Acetyl- L"

( i x ) FEATURE:
( A ) NAME/KEY: Peptide
( B ) LOCATION: 5
( D ) OTHER INFORMATION: /note="Peptide 5 wherein Xaa = O—CO—CH2—CCL3"

( i x ) FEATURE:
( A ) NAME/KEY: Peptide
( B ) LOCATION: 6
( D ) OTHER INFORMATION: /note="Peptide 6 wherein Xaa =L."

( i x ) FEATURE:
( A ) NAME/KEY: Peptide
( B ) LOCATION: 8
( D ) OTHER INFORMATION: /note="Peptide 8 wherein Xaa = beta- OtBu."

( i x ) FEATURE:
( A ) NAME/KEY: Peptide
( B ) LOCATION: 10
( D ) OTHER INFORMATION: /note="Peptide 10 wherein Xaa = gamma- OtBu."

( i x ) FEATURE:
( A ) NAME/KEY: Peptide
( B ) LOCATION: 13..16
( D ) OTHER INFORMATION: /note="Peptides 13-16 wherein Xaa = ( gamma - OtBu )-gamma-Aba-PAM."

( x i ) SEQUENCE DESCRIPTION: SEQ ID NO:2:

```
Xaa Xaa Xaa Tyr Xaa Xaa Asp Xaa Glu Xaa Gly Glu Xaa Xaa Xaa Xaa
1               5                   10                  15
```

( 2 ) INFORMATION FOR SEQ ID NO:3:

( i ) SEQUENCE CHARACTERISTICS:
( A ) LENGTH: 13 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..3
( D ) OTHER INFORMATION: /note="Peptides 1-3 wherein Xaa = N-Acetyl- L."

( i x ) FEATURE:
( A ) NAME/KEY: Peptide
( B ) LOCATION: 5
( D ) OTHER INFORMATION: /note="Peptide 5 wherein Xaa =L."

( i x ) FEATURE:
( A ) NAME/KEY: Peptide
( B ) LOCATION: 10..12
( D ) OTHER INFORMATION: /note="Peptides 10-12 wherein Xaa = gamma-Aba PAM."

( x i ) SEQUENCE DESCRIPTION: SEQ ID NO:3:

Xaa Xaa Xaa Xaa Tyr Xaa Asp Glu Gly Glu Xaa Xaa Xaa
1 5 10

( 2 ) INFORMATION FOR SEQ ID NO:4:

( i ) SEQUENCE CHARACTERISTICS:
( A ) LENGTH: 14 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1
( D ) OTHER INFORMATION: /note="Peptide 1 wherein Xaa = tBoc which is N-tert.-butoxycarbonyl."

( i x ) FEATURE:
( A ) NAME/KEY: Peptide
( B ) LOCATION: 3..13
( D ) OTHER INFORMATION: /note="Peptides 3, 7, 9 and 13 wherein Xaa =(OBz) wherein Bz =benzyl."

( i x ) FEATURE:
( A ) NAME/KEY: Peptide
( B ) LOCATION: 5..11
( D ) OTHER INFORMATION: /note="Peptides 5 and 11 wherein Xaa =(beta-COOTce) wherein Tce = — CH2CCl3(2,2,2-trichloroethyl."

( x i ) SEQUENCE DESCRIPTION: SEQ ID NO:4:

Xaa Thr Xaa Asp Xaa Thr Xaa Ser Xaa Asp Xaa Ser Xaa Xaa
1 5 10

( 2 ) INFORMATION FOR SEQ ID NO:5:

( i ) SEQUENCE CHARACTERISTICS:
( A ) LENGTH: 14 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1
( D ) OTHER INFORMATION: /note="Peptide 1 wherein Xaa =Ac which is CH3CO or C-14 CH3CO."

( i x ) FEATURE:
( A ) NAME/KEY: Peptide
( B ) LOCATION: 3..13
( D ) OTHER INFORMATION: /note="Peptides 3, 7, 9 and 13 wherein Xaa =OBz wherein Bz =benzyl."

( i x ) FEATURE:
( A ) NAME/KEY: Peptide
( B ) LOCATION: 5..11
( D ) OTHER INFORMATION: /note="Peptides 5 and 11 wherein Xaa =(beta-COOTce) wherein Tce =—CH2CCl3 (2,2,2-trichloroethyl)."

( i x ) FEATURE:
( A ) NAME/KEY: Peptide
( B ) LOCATION: 14
( D ) OTHER INFORMATION: /note="Peptide 14 wherein Xaa = Aba."

( x i ) SEQUENCE DESCRIPTION: SEQ ID NO:5:

-continued

Xaa Thr Xaa Asp Xaa Thr Xaa Ser Xaa Asp Xaa Ser Xaa Xaa
1 5 10

( 2 ) INFORMATION FOR SEQ ID NO:6:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1
( D ) OTHER INFORMATION: /note="Peptide 1 wherein Xaa =Ac which is CH3CO or C-14 CH3CO."

( i x ) FEATURE:
( A ) NAME/KEY: Peptide
( B ) LOCATION: 4..8
( D ) OTHER INFORMATION: /note="Peptides 4 and 8 wherein Xaa =(beta-COOTce) wherein Tce =CH2CCl3 (2,2,2-trichloroethyl)."

( i x ) FEATURE:
( A ) NAME/KEY: Peptide
( B ) LOCATION: 10
( D ) OTHER INFORMATION: /note="Peptide 10 wherein Xaa = Aba."

( i x ) FEATURE:
( A ) NAME/KEY: Peptide
( B ) LOCATION: 11
( D ) OTHER INFORMATION: /note="Peptide 11 wherein Xaa = OH."

( x i ) SEQUENCE DESCRIPTION: SEQ ID NO:6:

Xaa Thr Asp Xaa Thr Ser Asp Xaa Ser Xaa Xaa
1 5 10

( 2 ) INFORMATION FOR SEQ ID NO:7:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: -9
( D ) OTHER INFORMATION: /note="Peptide 1 wherein Xaa =Ac which is CH3CO or C-14 CH3CO."

( i x ) FEATURE:
( A ) NAME/KEY: Peptide
( B ) LOCATION: -6..-2
( D ) OTHER INFORMATION: /note="Peptides 4 and 8 wherein Xaa =(beta-COOTce) wherein Tce =—CH2CCl3 (2,2,2-trichloroethyl)."

( i x ) FEATURE:
( A ) NAME/KEY: Protein
( B ) LOCATION: 1
( D ) OTHER INFORMATION: /note="Peptide 10 wherein Xaa = Aba."

( i x ) FEATURE:
( A ) NAME/KEY: Peptide
( B ) LOCATION: 2
( D ) OTHER INFORMATION: /note="Peptide 11 wherein Xaa = OActive ester."

( x i ) SEQUENCE DESCRIPTION: SEQ ID NO:7:

Xaa Thr Asp Xaa Thr Ser Asp Xaa Ser Xaa Xaa
               - 5                          1

( 2 ) INFORMATION FOR SEQ ID NO:8:

( i ) SEQUENCE CHARACTERISTICS:
       ( A ) LENGTH: 11 amino acids
       ( B ) TYPE: amino acid
       ( C ) STRANDEDNESS: single
       ( D ) TOPOLOGY: linear ( i i ) MOLECULE TYPE: peptide ( i x ) FEATURE:
       ( A ) NAME/KEY: Peptide
       ( B ) LOCATION: 1
       ( D ) OTHER INFORMATION: /note="Peptide 1 wherein Xaa =Ac
             which is CH3CO or C-14 CH3CO."

( i x ) FEATURE:
       ( A ) NAME/KEY: Peptide
       ( B ) LOCATION: 4..8
       ( D ) OTHER INFORMATION: /note="Peptides 4 and 8 wherein
             Xaa =beta-COOH."

( i x ) FEATURE:
       ( A ) NAME/KEY: Peptide
       ( B ) LOCATION: 11
       ( D ) OTHER INFORMATION: /note="Peptide 11 wherein Xaa =
             CO—NH—Lys—Ab."

( x i ) SEQUENCE DESCRIPTION: SEQ ID NO:8:

Xaa Thr Asp Xaa Thr Ser Asp Xaa Ser Xaa Xaa
 1               5                        1 0

( 2 ) INFORMATION FOR SEQ ID NO:9:

( i ) SEQUENCE CHARACTERISTICS:
       ( A ) LENGTH: 13 amino acids
       ( B ) TYPE: amino acid
       ( C ) STRANDEDNESS: single
       ( D ) TOPOLOGY: linear ( i i ) MOLECULE TYPE: peptide ( i x ) FEATURE:
       ( A ) NAME/KEY: Peptide
       ( B ) LOCATION: 1
       ( D ) OTHER INFORMATION: /note="Peptide 1 wherein Xaa =
             Fmoc."

( i x ) FEATURE:
       ( A ) NAME/KEY: Peptide
       ( B ) LOCATION: 3
       ( D ) OTHER INFORMATION: /note="Peptide 3 wherein X -
             ( O — C O — T c e ) wherein Tce =—CH2CCl3 (2,2,2- trichloroethyl)."

( i x ) FEATURE:
       ( A ) NAME/KEY: Peptide
       ( B ) LOCATION: 5
       ( D ) OTHER INFORMATION: /note="Peptide 5 wherein X =
             beta- OtBu."

( i x ) FEATURE:
       ( A ) NAME/KEY: Peptide
       ( B ) LOCATION: 7..10
       ( D ) OTHER INFORMATION: /note="Peptides 7 and 10 wherein
             Xaa =(gamma-OtBu)."

( i x ) FEATURE:
       ( A ) NAME/KEY: Peptide
       ( B ) LOCATION: 11..13
       ( D ) OTHER INFORMATION: /note="Peptides 11-13 wherein Xaa
             =   gamma-Aba-PAM."

( x i ) SEQUENCE DESCRIPTION: SEQ ID NO:9:

Xaa Tyr Xaa Asp Xaa Glu Xaa Gly Glu Xaa Xaa Xaa Xaa
1               5                       10

( 2 ) INFORMATION FOR SEQ ID NO:10:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /note="Peptide 1 wherein Xaa =Ac
            which is CH3CO or C-14 CH3CO."

( i x ) FEATURE:
        ( A ) NAME/KEY: Peptide
        ( B ) LOCATION: 3
        ( D ) OTHER INFORMATION: /note="Peptide 3 wherein Xaa =
        ( O — C O — T c e ) wherein Tce =CH2CCl3 (2,2,2- trichloroethyl)."

( i x ) FEATURE:
        ( A ) NAME/KEY: Peptide
        ( B ) LOCATION: 5
        ( D ) OTHER INFORMATION: /note="Peptide 5 wherein Xaa =
            ( b e t a - O t B u )."

( i x ) FEATURE:
        ( A ) NAME/KEY: Peptide
        ( B ) LOCATION: 7..10
        ( D ) OTHER INFORMATION: /note="Peptides 7 and 10 wherein
            Xaa =(gamma-OtBu)."

( i x ) FEATURE:
        ( A ) NAME/KEY: Peptide
        ( B ) LOCATION: 11..13
        ( D ) OTHER INFORMATION: /note="Peptides 11-13 wherein Xaa
            =    gamma-Aba-PAM."

( x i ) SEQUENCE DESCRIPTION: SEQ ID NO:10:

Xaa Tyr Xaa Asp Xaa Glu Xaa Gly Glu Xaa Xaa Xaa Xaa
1               5                       10

( 2 ) INFORMATION FOR SEQ ID NO:11:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /note="Peptide 1 wherein Xaa =Ac
            which is CH3CO or C-14 CH3CO."

( i x ) FEATURE:
        ( A ) NAME/KEY: Peptide
        ( B ) LOCATION: 3
        ( D ) OTHER INFORMATION: /note="Peptide 3 wherein Xaa =
        ( O — C O — T c e ) wherein Tce =CH2CCl3 (2,2,2- trichloroethyl)."

( i x ) FEATURE:
        ( A ) NAME/KEY: Peptide
        ( B ) LOCATION: 8..10
        ( D ) OTHER INFORMATION: /note="Peptides 8-11 wherein Xaa =
            gamma-Aba- PAM."

( x i ) SEQUENCE DESCRIPTION: SEQ ID NO:11:

Xaa Tyr Xaa Asp Glu Gly Glu Xaa Xaa Xaa
1 5 10

( 2 ) INFORMATION FOR SEQ ID NO:12:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1
( D ) OTHER INFORMATION: /note="Peptide 1 wherein Xaa =Ac which is CH3CO or C-14 CH3CO."

( i x ) FEATURE:
( A ) NAME/KEY: Peptide
( B ) LOCATION: 3
( D ) OTHER INFORMATION: /note="Peptide 3 wherein Xaa is ( O — CO — Tcc ) wherein Tcc =CH2CCl3 (2,2,2- trichloroethyl)."

( i x ) FEATURE:
( A ) NAME/KEY: Peptide
( B ) LOCATION: 8..10
( D ) OTHER INFORMATION: /note="Peptides 8-10 wherein Xaa = gamma-Aba- OH."

( x i ) SEQUENCE DESCRIPTION: SEQ ID NO:12:

Xaa Tyr Xaa Asp Glu Gly Glu Xaa Xaa Xaa
1 5 10

( 2 ) INFORMATION FOR SEQ ID NO:13:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1
( D ) OTHER INFORMATION: /note="Peptide 1 wherein Xaa =Ac which is CH3CO or C-14 CH3CO."

( i x ) FEATURE:
( A ) NAME/KEY: Peptide
( B ) LOCATION: 3
( D ) OTHER INFORMATION: /note="Peptide 3 wherein Xaa = ( O — CO — Tcc ) wherein Tcc =CH2CCl3 (2,2,2- trichloroethyl)."

( i x ) FEATURE:
( A ) NAME/KEY: Peptide
( B ) LOCATION: 8..9
( D ) OTHER INFORMATION: /note="Peptides 8-9 wherein Xaa = gamma- Aba."

( x i ) SEQUENCE DESCRIPTION: SEQ ID NO:13:

Xaa Tyr Xaa Asp Glu Gly Glu Xaa Xaa
1 5

( 2 ) INFORMATION FOR SEQ ID NO:14:

( i ) SEQUENCE CHARACTERISTICS:
( A ) LENGTH: 8 amino acids
( B ) TYPE: amino acid
( C ) STRANDEDNESS: single -continued ( D ) TOPOLOGY: linear ( i i ) MOLECULE TYPE: peptide ( i x ) FEATURE:
( A ) NAME/KEY: Peptide
( B ) LOCATION: 1
( D ) OTHER INFORMATION: /note="Peptide 1 wherein Xaa =Ac which is CH3CO or C-14 CH3CO."

( i x ) FEATURE:
( A ) NAME/KEY: Peptide
( B ) LOCATION: 7..8
( D ) OTHER INFORMATION: /note="Peptides 7-8 wherein Xaa is gamma- Aba."

( x i ) SEQUENCE DESCRIPTION: SEQ ID NO:14:

```
Xaa Tyr Asp Glu Gly Glu Xaa Xaa
1               5
```

( 2 ) INFORMATION FOR SEQ ID NO:15:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1..6
( D ) OTHER INFORMATION: /note="Peptides 1-6 wherein Xaa = N-Acetyl-[L—Tyr—L—Asp—LGlu—Gly—Glu]n-gamma-Aba-PAM."

( x i ) SEQUENCE DESCRIPTION: SEQ ID NO:15:

```
Xaa Xaa Xaa Xaa Xaa Xaa
1               5
```